US010647461B2

(12) United States Patent
Altmann et al.

(10) Patent No.: US 10,647,461 B2
(45) Date of Patent: May 12, 2020

(54) METHODS AND APPARATUS FOR CLEANSING AND PACKAGING MEDICAL INSTRUMENTS OR THE LIKE

(71) Applicant: Biosense Webster (Israel) Ltd., Yokneam (IL)

(72) Inventors: Andres Claudio Altmann, Haifa (IL); Assaf Govari, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 339 days.

(21) Appl. No.: 15/602,739

(22) Filed: May 23, 2017

(65) Prior Publication Data

US 2018/0339797 A1    Nov. 29, 2018

(51) Int. Cl.
| | |
|---|---|
| *B65B 55/18* | (2006.01) |
| *A61L 2/14* | (2006.01) |
| *A61L 2/20* | (2006.01) |
| *A61L 2/26* | (2006.01) |
| *B65B 55/02* | (2006.01) |
| *B08B 5/02* | (2006.01) |
| *B08B 3/02* | (2006.01) |
| *A61L 2/22* | (2006.01) |
| *A61B 50/30* | (2016.01) |

(52) U.S. Cl.
CPC ............. *B65B 55/18* (2013.01); *A61L 2/14* (2013.01); *A61L 2/20* (2013.01); *A61L 2/202* (2013.01);
(Continued)

(58) Field of Classification Search
CPC .... A61L 2202/17; A61L 2202/15; A61L 2/14; A61L 2/26; B65B 55/18; B65B 55/027; B08B 3/022
(Continued)

(56) References Cited

U.S. PATENT DOCUMENTS 5,269,680 A    12/1993    Kawaguchi
5,451,368 A    9/1995    Jacob
(Continued)

FOREIGN PATENT DOCUMENTS

DE    2712020 A1    9/1978
EP    0685399 A1    12/1995
(Continued)

OTHER PUBLICATIONS

Extended European Search Report dated Oct. 15, 2018 for the European Patent Application No. 18173519.2.

*Primary Examiner* — Robert F Long
*Assistant Examiner* — Xavier A Madison
(74) *Attorney, Agent, or Firm* — Volpe and Koenig, P.C.

(57) ABSTRACT

A cleansing and packaging system for pipeline preparation of specialty medical instruments and method for cleansing and packaging instruments are provided herein. The cleansing and packaging system includes a first sealable cleansing compartment and a second sealable packaging compartment. A conveyor device transports medical instruments to be cleansed through a sealing entry door to the cleansing compartment, then to the packaging compartment through a sealing joining door, and then out of the packaging compartment through a sealing exit door. The cleansing compartment includes a sanitation system and a sterilization system, each which includes its own inspection devices that operate continuously to confirm the success of sanitation and sterilization operations. The packaging compartment includes a packaging system, which may include its own inspection devices that operate continuously to confirm the quality of the packaging of medical instruments. The pipeline approach provides greater availability of limited specialty medical instruments to hospital physicians.

34 Claims, 13 Drawing Sheets

(52) U.S. Cl.
CPC ............... *A61L 2/204* (2013.01); *A61L 2/206* (2013.01); *A61L 2/208* (2013.01); *A61L 2/22* (2013.01); *A61L 2/26* (2013.01); *B08B 3/022* (2013.01); *B08B 5/023* (2013.01); *B65B 55/027* (2013.01); *A61B 50/30* (2016.02); *A61L 2202/15* (2013.01); *A61L 2202/17* (2013.01); *A61L 2202/24* (2013.01)

(58) Field of Classification Search
USPC .......................................................... 53/428
See application file for complete search history.

(56) References Cited

U.S. PATENT DOCUMENTS

| | | | |
|---|---|---|---|
| 5,464,580 A * | 11/1995 | Popescu | B65B 55/18 422/1 |
| 5,732,529 A | 3/1998 | Dey et al. | |
| 5,987,855 A | 11/1999 | Dey et al. | |
| 2005/0135965 A1 | 6/2005 | Williams et al. | |
| 2009/0283517 A1 * | 11/2009 | Mackay | H05B 6/782 219/700 |
| 2013/0156640 A1 | 6/2013 | Kohler et al. | |
| 2014/0072683 A1 * | 3/2014 | Munger | A23L 6/782 219/700 |
| 2015/0374868 A1 | 12/2015 | Bruce et al. | |
| 2016/0074546 A1 | 3/2016 | Rizzone | |
| 2017/0007729 A1 * | 1/2017 | Bertomeu Asategui | A23L 3/04 |
| 2017/0066020 A1 | 3/2017 | Lapointe et al. | |

FOREIGN PATENT DOCUMENTS

| | | |
|---|---|---|
| JP | 2013-186009 A | 9/2013 |
| WO | 2015094122 A1 | 6/2015 |
| WO | 2016/009204 A1 | 1/2016 |

* cited by examiner

METHODS AND APPARATUS FOR CLEANSING AND PACKAGING MEDICAL INSTRUMENTS OR THE LIKE

SUMMARY

Methods and apparatus for cleansing and packaging items, such as medical instruments or the like, are provided. A first sealable compartment houses a cleansing device. A second sealable compartment joined to the first compartment houses a packaging device. A conveyor device is configured to selectively transport items to be cleansed and packaged through the first compartment and second compartment. The conveyor and sealable compartments are configured to convey an item to be cleansed and packaged into the first compartment to a cleansing position where the first compartment is sealed from external contamination for the cleansing device to cleanse the conveyed item. The conveyor and compartments are configured to convey the cleansed item from the first compartment directly into the second compartment where the second compartment is sealed from external contamination for the packaging device to package the cleansed item. The conveyor and compartments are configured to convey the cleansed and packaged item from the second compartment.

In a preferred embodiment, the first compartment is preferably configured with a sealing entry door component. The second compartment is preferably configured with a sealing exit door component. A sealing joining door component is preferably provided for communication between the first and second compartments. The entry door component is configured to open for conveying an item to the cleansing position and to sealingly close when the item is disposed at the cleansing position. The joining door component is configured to be sealingly closed when the item is disposed at the cleansing position and during cleansing and to open for conveying a cleansed item into the packaging compartment. The exit door component is configured to be sealingly closed during packaging of the item and to open to permit the cleansed, packaged item to exit.

The cleansing device preferably includes a sanitation device and a sterilization device, wherein the sterilization device includes one or more of a hydrogen peroxide gas plasma sterilization system, an ethylene oxide gas sterilization system, an ozone gas sterilization system, a nitrogen dioxide gas sterilization system, a hydrogen peroxide gas sterilization system, a peracetic acid gas sterilization system, a formaldehyde gas sterilization system, or a glutaraldehyde gas sterilization system.

In another embodiment, the cleansing device includes a plurality of cleansing nozzles for spraying at least one solution onto an item disposed at the cleansing position.

In yet another embodiment, the cleansing device includes a sanitation device and a sterilization device where the sanitation device includes a plurality of sanitation nozzles configured for spraying at least one solution onto an item disposed at the cleansing position, and/or the sterilization device includes a plurality of sterilization nozzles configured for spraying at least one solution onto an item disposed at the cleansing position.

In yet another embodiment, the cleansing device includes a sanitation device and a sterilization device where the sanitation device includes a drying device configured to dry an item and the sanitation device is operable to dry an item before and/or after a sanitation operation, and/or the sterilization device includes a drying device configured to dry an item and the sterilization device is operable to dry an item before and/or after a sterilization operation.

In yet another embodiment, the packaging device includes a drying device configured to dry an item and the packaging device is operable to dry an item before and/or after a packaging operation.

In another embodiment, the cleansing device includes cleansing sensors configured to detect cleansing defects and the cleansing device is operable to sense cleansing defects of an item after a cleansing operation and to conduct a further cleansing operation if a cleansing defect is sensed.

In another embodiment, the cleansing device includes a sanitation device and a sterilization device where the sanitation device includes sanitation sensors configured to detect sanitation defects and the sanitation device is operable to sense sanitation defects of an item after a sanitation operation and to conduct a further sanitation operation if a sanitation defect is sensed, and/or the sterilization device includes sterilization sensors configured to detect sterilization defects and the sterilization device is operable to sense sterilization defects of an item after a sterilization operation and to conduct a further sterilization operation if a sterilization defect is sensed. In one aspect, the sanitation device includes a rotational mount configured to hold the sanitation sensors and the sanitation device is operable to continuously rotate the mount holding the sanitation sensors 360 degrees during a sanitation operation. In another aspect, the sterilization device includes a rotational mount configured to hold the sterilization sensors and the sterilization device is operable to continuously rotate the mount holding the sterilization sensors 360 degrees during a sterilization operation.

Also provided herein are methods for cleansing and packaging items, such as medical instruments or the like. A first sealable compartment housing a cleansing device and a second sealable compartment joined to the first compartment housing a packaging device are provided along with a conveyor device configured to selectively transport items to be cleansed and packaged through the first compartment and second compartment. An item to be cleansed and packaged is conveyed into the first compartment to a cleansing position where the first compartment is sealed from external contamination for the cleansing device to cleanse the conveyed item. The cleansed item is conveyed from the first compartment directly into the second compartment where the second compartment is sealed from external contamination for the packaging device to package the cleansed item. The cleansed and packaged item is then conveyed from the second compartment.

In a preferred embodiment, the method is conducted where the first compartment is configured with a sealing entry door component, the second compartment is configured with a sealing exit door component, and a sealing joining door component is provided for communication between the first and second compartments. In such case the method preferably includes opening the entry door component for conveying an item to the cleansing position and sealingly closing the entry door component when the item is disposed at the cleansing position. The joining door component is sealingly closed when the item is disposed at the cleansing position and during cleansing. The joining door component is then opened for conveying a cleansed item into the second compartment. The exit door component is sealingly closed during packaging. The exit door component is then opened to permit the cleansed, packaged item to exit.

In another embodiment, the cleansing device includes a sanitation device and a sterilization device, where the sterilization device includes one or more of a hydrogen peroxide gas plasma sterilization system, an ethylene oxide gas sterilization system, an ozone gas sterilization system, a nitrogen dioxide gas sterilization system, a hydrogen peroxide gas sterilization system, a peracetic acid gas sterilization system, a formaldehyde gas sterilization system, or a glutaraldehyde gas sterilization system. The method can include conducting a sanitation operation followed by a sterilization operation to cleanse an item disposed at the cleansing position.

In another embodiment, where the cleansing device includes a plurality of cleansing nozzles configured to spray at least one solution onto an item disposed at the cleansing position, the method can include spraying at least one solution onto an item disposed at the cleansing position during a cleansing operation.

In another embodiment, where the cleansing device includes a sanitation device and/or a sterilization device, the sanitation device includes a plurality of sanitation nozzles configured for spraying at least one solution onto an item disposed at the cleansing position and/or the sterilization device includes a plurality of sterilization nozzles configured for spraying at least one solution onto an item disposed at the cleansing position, the method can include conducting a sanitation operation followed by a sterilization operation to cleanse an item disposed at the cleansing position; spraying at least one solution onto an item disposed at the cleansing position during a sanitation operation; and/or spraying at least one solution onto an item disposed at the cleansing position during a sterilization operation.

In yet another embodiment, where the cleansing device includes a sanitation device and a sterilization device, the sanitation device includes a drying device configured to dry an item disposed at the cleansing position and/or the sterilization device includes a drying device configured to dry an item disposed at the cleansing position, the method can include conducting a sanitation operation followed by a sterilization operation to cleanse an item disposed at the cleansing position; drying an item disposed at the cleansing position before and/or after a sanitation operation; and/or drying an item disposed at the cleansing position before and/or after a sterilization operation.

In yet another embodiment, where the packaging device includes a drying device configured to dry an item in the second compartment, the method can include conducting a packaging operation to package an item in the second compartment and drying an item in the second compartment before and/or after a packaging operation.

In yet another embodiment, where the cleansing device includes cleansing sensors configured to detect cleansing defects, the method can include sensing cleansing defects of an item after a cleansing operation and conducting a further cleansing operation if a cleansing defect is sensed.

In yet another embodiment, where the cleansing device includes a sanitation device and/or a sterilization device, the sanitation device includes sanitation sensors configured to detect sanitation defects and/or the sterilization device includes sterilization sensors configured to detect sterilization defects, further the method can include conducting a sanitation operation followed by a sterilization operation to cleanse an item disposed at the cleansing position; sensing sanitation defects of an item after a sanitation operation and conducting a further sanitation operation if a sanitation defect is sensed; and/or sensing sterilization defects of an item after a sterilization operation and conducting a further sterilization operation if a sterilization defect is sensed.

In yet another embodiment, where the sanitation device includes a rotational mount configured to hold the sanitation sensors and/or the sterilization device includes a rotational mount configured to hold the sterilization sensors, the method can include rotating the mount holding the sanitation sensors 360 degrees continuously during a sanitation operation and/or rotating the mount holding the sterilization sensors 360 degrees continuously during a sterilization operation.

These and other objects, features and advantages of the present invention will be apparent from the following detailed description of illustrative embodiments thereof, which is to be read in connection with the accompanying drawings.

BRIEF DESCRIPTION OF THE DRAWINGS

The present invention is illustrated by way of example, and not by way of limitation, in the figures of the accompanying drawings in which.

DETAILED DESCRIPTION

Figure 1:
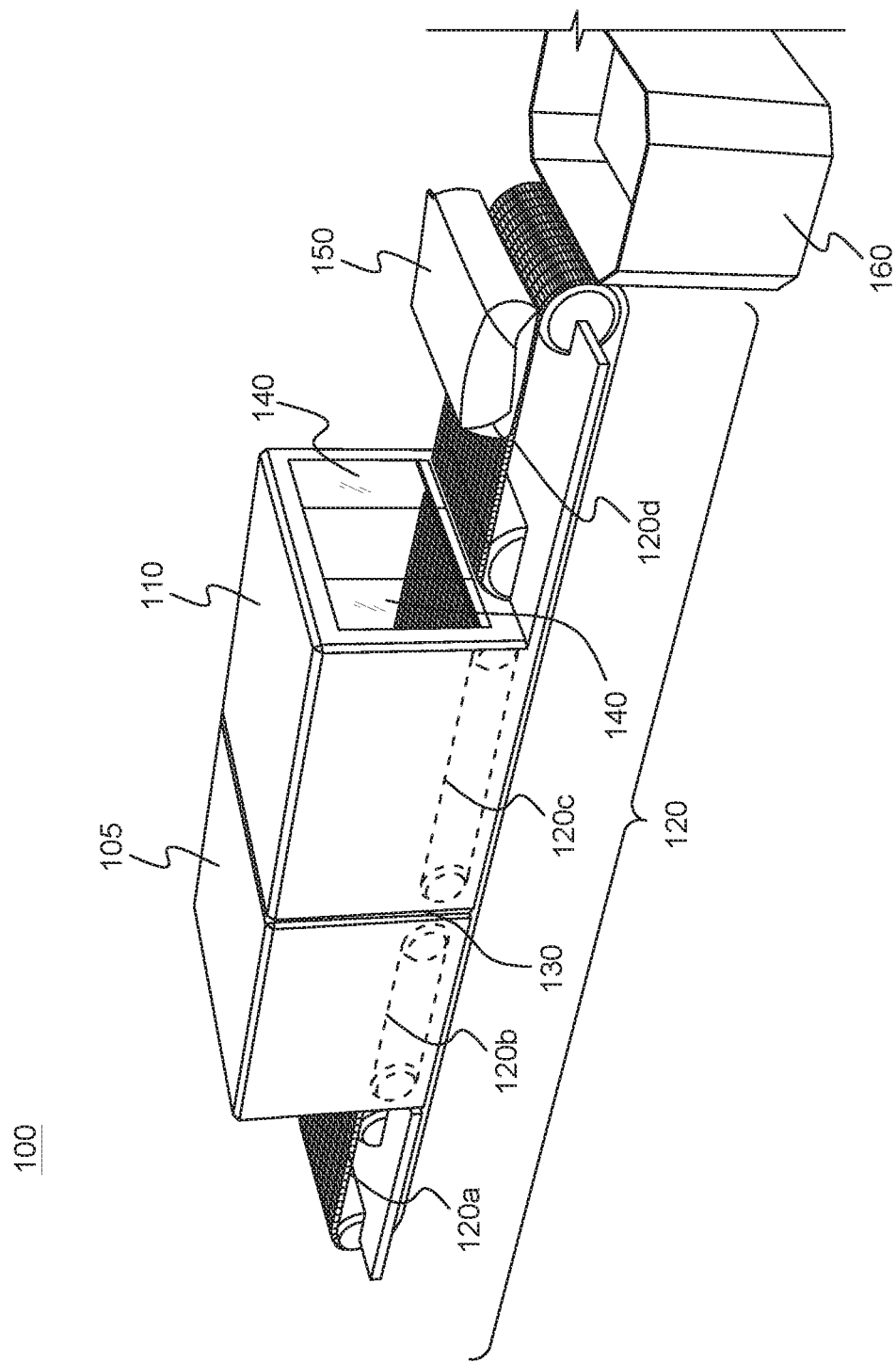
FIG. 1 is an illustration of an embodiment according to the invention showing cleansed and packaged instruments exiting from a cleansing and packaging apparatus.

The present invention is directed to methods and apparatus related to reusable medical instruments or the like and the cleansing and packaging thereof.

In the area of reusable medical instruments, sanitation, sterilization and packaging are intuitively related processes, but in current practice, their combination is inefficient and time consuming. Hospital operating rooms face limited supply and high demand for expensive medical instruments, such as endoscopes, which are not readily available due to presently obsolete processing chains. The inventors have recognized that it would be advantageous to implement a system for the seamless integration of sanitation, sterilization and packaging that eliminates the limitations of current practices, as detailed in the following paragraphs.

Currently, the processes for sanitation, sterilizing and packaging of an instrument in preparation for its subsequent use involve slow turnover with unnecessary risk of contamination. For example, contamination occurs during packaging when the sterilized instruments are manually exposed to external contamination in the outside air after a sterilization operation. Further, the inventors have recognized that speed and the amount of sterilization material are compromised by using a wrapped tray to hold instruments during sterilization. Covering the tray during sterilization, particularly during hydrogen peroxide gas plasma sterilization, necessitates both additional time and more sterilization material to enable the sterilant to penetrate the covering on the instruments.

In regard to the sterilization process, one skilled in the art will recognize that there are several methods to sterilize a medical instrument. Conventional sterile processing procedures for medical instruments involve high temperature systems, such as steam and dry heat units, or chemicals, such as ethylene oxide gas, nitrogen dioxide gas, or ozone gas. It is known to sterilize instruments with a vaporized chemical sterilant, such as hydrogen peroxide, peracetic acid, glutaraldehyde and formaldehyde. In particular, a hydrogen peroxide gas plasma sterilization system comprises a vacuum chamber, source of hydrogen peroxide vapor and a source of radio frequency energy to create a plasma. Sterilization with hydrogen peroxide involves low pressure and low temperature sterilization cycles that are optimal for sterilizing medical instruments that are sensitive to heat.

In general, reusable instruments are typically composed of stainless steel material and are typically sterilized before their initial use and then cleaned, sanitized and resterilized prior to each subsequent use. The sterilization process generally involves placing instruments to be sterilized in a tray, wrapping the instruments and the tray with a sterilization wrap and placing the wrapped tray and instruments in a sterilization chamber where the instruments are exposed to a sterilant. Currently, the instruments are placed in a tray and wrapped before initiating exposure to the sterilant.

Certain reusable instruments, such as flexible endoscopes, may only be sanitized and are not subjected to high-temperature sterilization due to their fragile components. These endoscopes are usually cleaned using only a manual sanitation process, which is cumbersome as it requires an effective set-up and supplies to sanitize the endoscope. A more efficient means of sanitizing, sterilizing and packaging such specialty instruments is required.

The inventors have recognized that it would be advantageous to combine the sanitation, sterilization and packaging processes into one hermetic, pipeline conveyor process, where the entire process occurs within sealed compartments, without any exposure to microbial elements from outside air. Such a system would save time and sterilization material. Further, the inventors have recognized that such a system would achieve greater efficiency in the supply of sterile endoscopes, for example, and other essential specialty instruments. The inventors have recognized that it would be advantageous to cleanse one endoscope simultaneously while another is packaged, thereby expediting the delivery of essential surgical instruments to hospital physicians.

Various embodiments of the invention are described in the following paragraphs. Where like elements have been depicted in multiple embodiments, identical or similar reference numerals have been used for ease of understanding.

Referring to FIG. 1, an example cleansing and packaging system 100 is depicted that provides an improved sanitation, sterilization and packaging process for surgical instruments or the like and eliminates the potential for contamination due to exposure to microbial elements in unsealed conditions. The example cleansing and packaging system 100 has a sealable cleansing compartment 105 and a sealable packaging compartment 110. Preferably, the sealable compartments 105 and 110 are maintained free from the microbial content of the outside environment, including air and other elements that are external thereto. It is understood that the microbial-free aspect of the compartments 105 and 110, may be achieved by alternative embodiments, including a clean room or other cleansing and packaging system mechanism that encases the entire system 100.

The cleansing compartment 105 and the packaging compartment 110 are preferably joined contiguously to each other as shown in the example cleansing and packaging system 100, but may be disposed serially without being physically connected. In the depicted example, the cleansing compartment 105 includes both a sanitation system and a sterilization system and the packaging compartment 110 includes a packaging system. Of course, in another embodiment, the cleansing compartment 105 may just include a sterilization system in conjunction with the packaging system of the packaging compartment 110.

In addition, the example cleansing and packaging system 100 has a conveyor system 120 partially encased by and configured to transport items through the compartments 105 and 110. As illustrated in FIG. 1, the conveyor system 120 has four individual conveyor sections, 120a, 120b, 120c and 120d. Although the conveyor system 120 has been illustrated with these four individual conveyor sections 120a, 120b, 120c and 120d, it is understood that other embodiments of the cleansing and packaging system 100 may utilize one, single conveyor section or any other number of individual conveyor sections. Referring to FIG. 1, in general, the conveyor system 120 enters the cleansing compartment 105, runs first through the cleansing compartment 105, then through the packaging compartment 110, and then finally out of the packaging compartment 110. In particular, conveyor section 120a resides outside the entrance of the cleansing compartment 105, conveyor section 120b is encased by and configured to transport items through the cleansing compartment 105, conveyor section 120c is encased by and configured to transport items through the packaging compartment 110, and conveyor section 120d resides outside the exit of the packaging compartment 110. Thus, conveyor section 120a is configured to convey an instrument to the entrance of the cleansing compartment 105, where conveyor section 120b is configured to receive the instrument from conveyor section 120a. Conveyor section 120b is further configured to convey the instrument through the cleansing compartment 105 to the exit of the cleansing compartment 105 and entrance of the packaging compartment 110. It follows that conveyor section 120c is configured to receive the instrument from conveyor section 120b. Conveyor section 120c is further configured to convey the instrument through the packaging compartment 110 to the exit of the packaging compartment 110. Finally, conveyor section 120d is configured to receive a wrapped packaged 150 from conveyor section 120c and convey the wrapped package 150 out of the packaging compartment 110 to a container 160.

Figure 3:
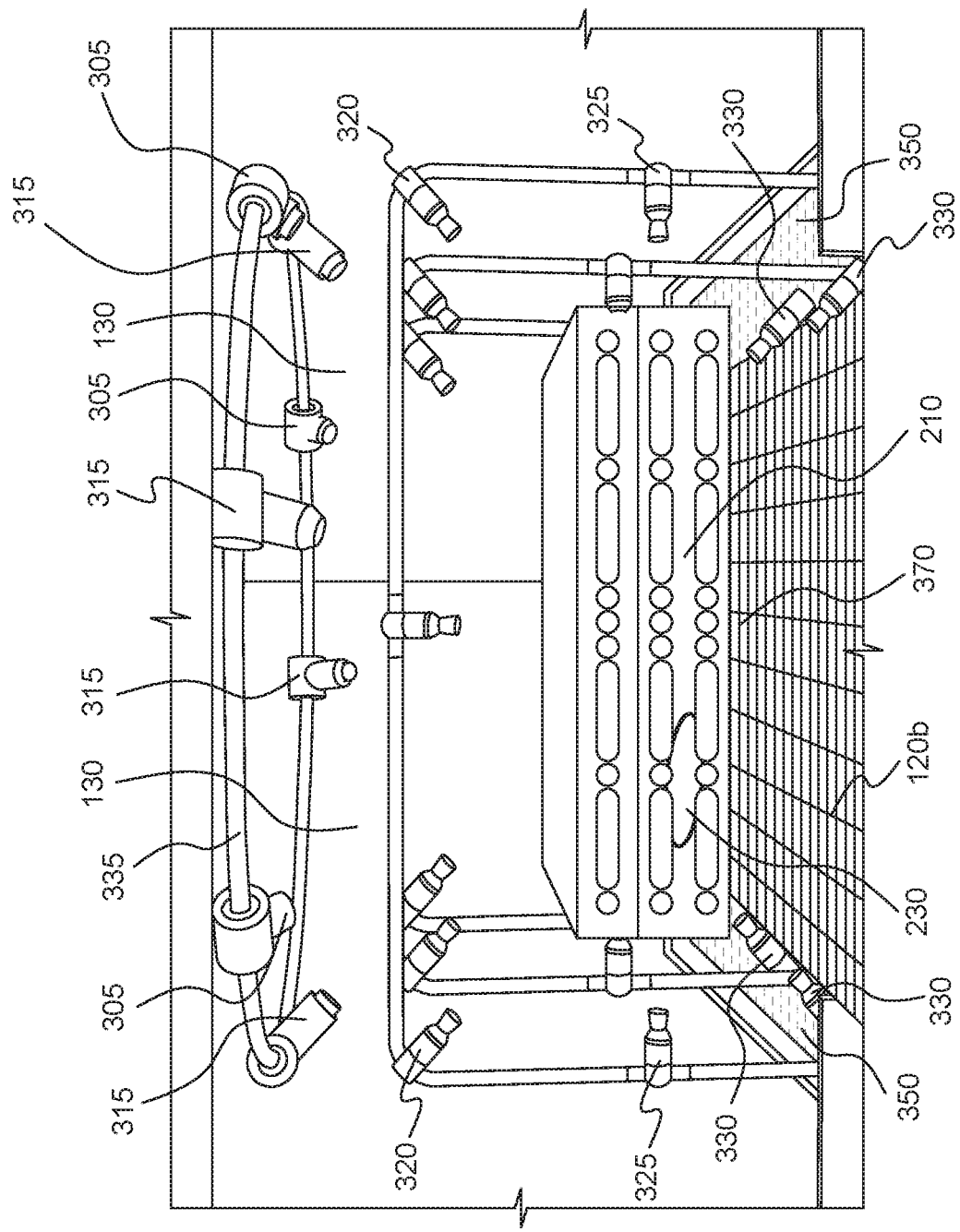
FIG. 3 is an illustration of the embodiment shown in FIG. 1, showing the instrument in the tray on the conveyor that has entered a first sealable compartment at a cleansing position for cleansing.
Figure 4:
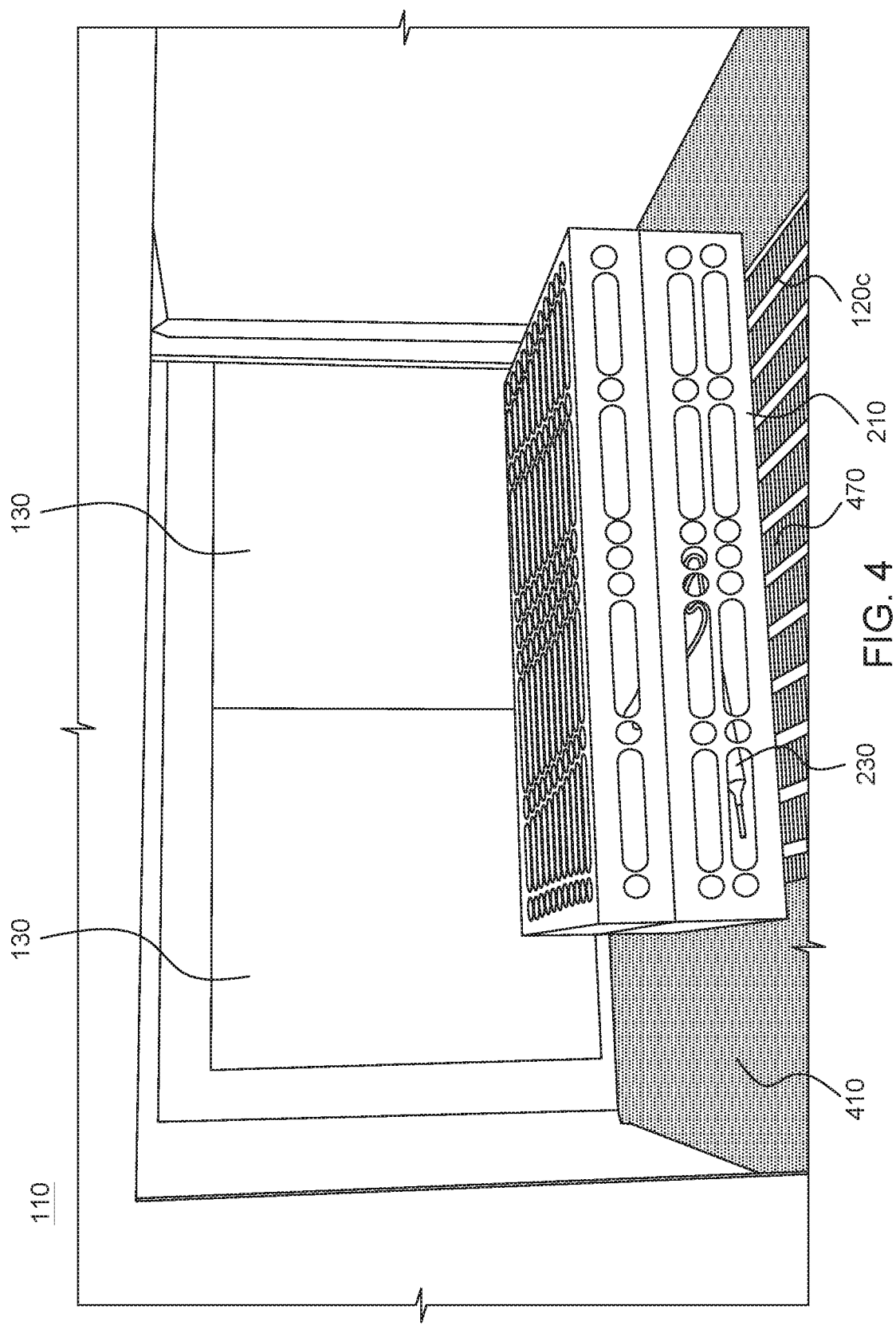
FIG. 4 is an illustration of the embodiment shown in FIG. 1, showing the instrument in the tray on the conveyor that has entered a second sealable compartment at a packaging position for packaging.

Further, the conveyor system 120 delivers instruments to specific positions in the compartments 105 and 110. More specifically, as shown in FIG. 3, the cleansing compartment 105 features a cleansing position 370 for cleansing an instrument. The conveyor system 120 enters the cleansing compartment 105 to deliver an instrument to the cleansing position 370 for cleansing. At the cleansing position 370, conveyor section 120b will momentarily stop conveying in coordination with a cleansing operation in the cleansing compartment 105. Similarly, as shown in FIG. 4, the packaging compartment 110 features a packaging position 470 for packaging an instrument. The conveyor system 120 enters the packaging compartment 110 to deliver an instrument to the packaging position 470 for packaging. At the packaging position 470, conveyor section 120c will momentarily stop conveying in coordination with a packaging operation in the packaging compartment 110.

Figure 2:
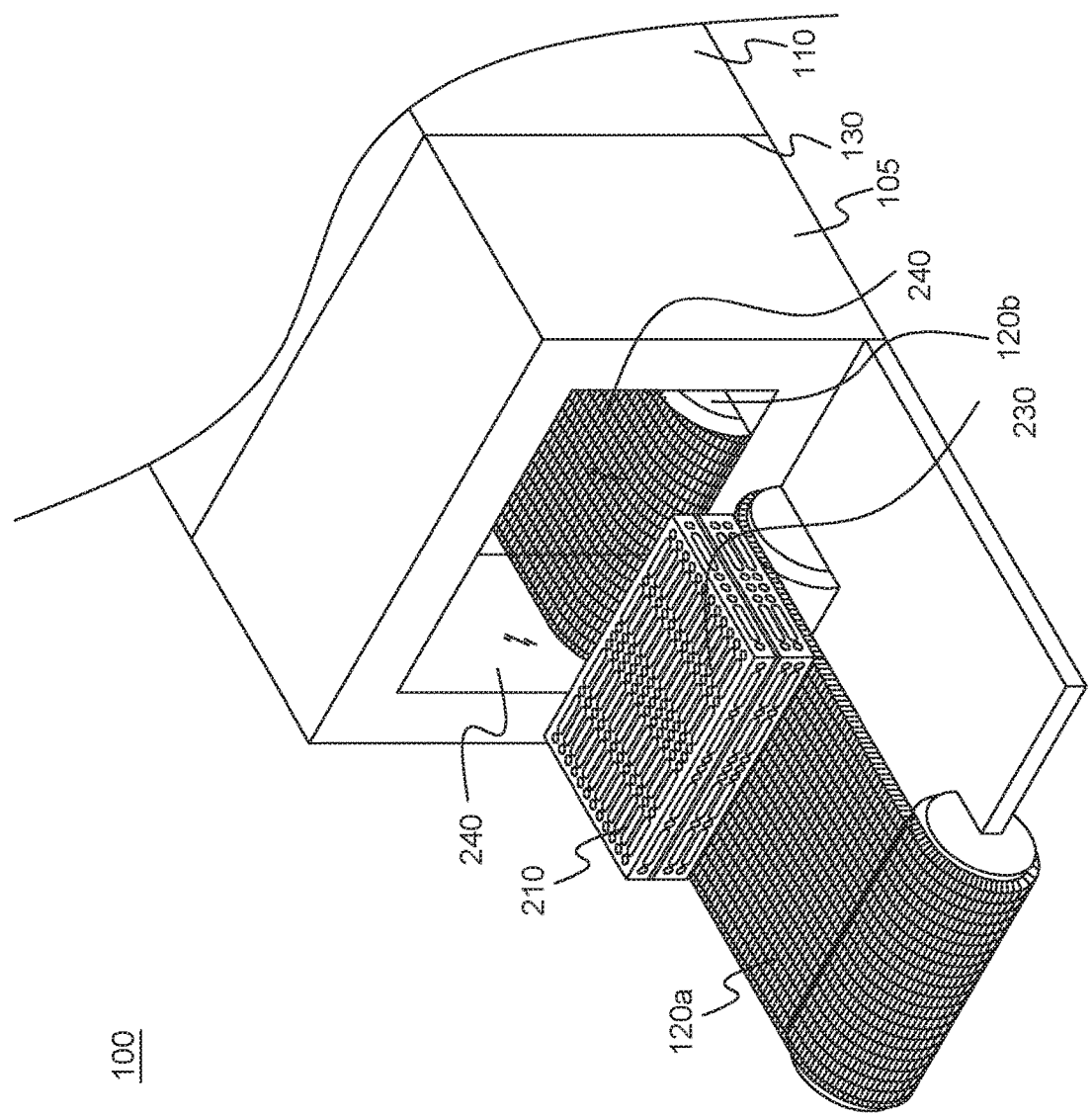
FIG. 2 is an illustration of the embodiment shown in FIG. 1, showing the instrument to be cleansed and packaged in a tray on a conveyor before it enters a first compartment for cleansing.

Further, the example cleansing and packaging system 100 features three sets of sealing doors. Referring to FIG. 2, a perspective view of the example cleansing and packaging system 100 is shown. A first set of sealing doors is configured at the entry of the cleansing compartment 105 to provide a sealing entry door component 240. A second set of sealing doors is configured between the cleansing compartment 105 and the packaging compartment 110 to provide a sealing joining door component 130, also shown in FIGS. 3 and 4. A third set of sealing doors is configured at the exit of the packaging compartment 110 to provide a sealing exit door component 140, as shown in FIG. 1. For each of the three aforementioned sets of sealing doors, the sealing aspect can include one or both of a liquid seal and an air-tight seat Further, the three sets of sealing doors—the entry door component 240, the joining door component 130, and the exit door component 140—are preferably made of a transparent material that provides for vision into the cleansing compartment 105 and the packaging compartment 110 when the three sets of sealing doors are closed. While the three sets of sealing doors are preferably made of a transparent material, it is not necessary for them to be made of such transparent material.

Referring to FIGS. 1 and 2, the three sets of sealing doors, 240, 130 and 140 are preferably configured to permit the conveyor system 120 to transport the medical instrument being cleansed and packaged within the compartments 105 and 110 of the cleansing and packaging system 100 while maintaining sealing from external microbial contamination. To achieve one or both of a liquid seal and an air-tight seal, the three sets of sealing doors, 240, 130 and 140 are each configured to open from and close into a native seal with a gasket. In addition, the three sets of sealing doors, 240, 130 and 140 open and sealingly close in coordination with the four individual conveyor sections 120a, 120b, 120c and 120d. For example, the sealing entry door component 240 may open and sealingly close between conveyor sections 120a and 120b, the sealing joining door component 130 may open and sealingly close between conveyor sections 120b and 120c, and the sealing exit door component 140 may open and sealingly close between conveyor sections 120c and 120d. Further, it is understood that the three sets of sealing doors, 240, 130 and 140 can be configured to open and sealingly close based upon a variety of mechanisms, including opening horizontally from the sides or vertically from the top, by either rolling or sliding, for example. It is further understood that regardless of the mechanism utilized to open and sealingly close the three sets of sealing doors, 240, 130 and 140, one or both of a liquid seal and an air-tight seal is achieved when a sealing door, 240, 130 and 140, closes.

As aforementioned, while the conveyor system 120 of FIG. 1 has been illustrated with four individual conveyor sections 120a, 120b, 120c and 120d, it is understood that other embodiments of the cleansing and packaging system 100 may utilize one, single conveyor section or any other number of conveyor sections. In an alternative embodiment with one, single conveyor section running through the entire cleansing and packaging system 100, the conveyor 120 is preferably made of a substance, such as rubber, that enables the three sets of sealing doors, 240, 130 and 140, to sealingly engage the conveyor 120 when the sealing doors are closed. In particular, the conveyor 120 can have grooves with gaskets that provide for a vacuum seal when engaged by the sealing doors. Depending on the level and method of sterilization, the doors can, in another embodiment, be heavy drapes that prevent air movement. Such heavy drapes can be disposed at the entry of the cleansing compartment 105, between the cleansing compartment 105 and the packaging compartment 110, and at the exit of the packaging compartment 110.

Further, in reference to FIGS. 1 and 2, the opening and closing of the three sets of sealing doors, 240, 130 and 140, can be coordinated to keep external contaminants out of the example cleansing and packaging system 100. For example, at all times when the sealing entry door component 240 is open, the sealing joining door component 130 may always be closed, to prevent external air from entering the packaging compartment 110. Similarly, at all times when the sealing joining door component 130 is open, both the sealing entry door component 240 and sealing exit door component 140 may be closed. Finally, at all times when the sealing exit door component 140 is open, the sealing joining door component 130 may be closed to prevent external air from entering the cleansing compartment 105. Coordination of the three sets of sealing doors can enable the cleansing and packaging system 100 to cleanse one instrument 230 simultaneously while another instrument 230 is packaged, thereby maintaining the sterile environment inside the system 100. Alternatively, the system 100 can be operated to cleanse and then package one medical instrument at a time while maintaining the sterile environment inside the system 100.

Figure 10:
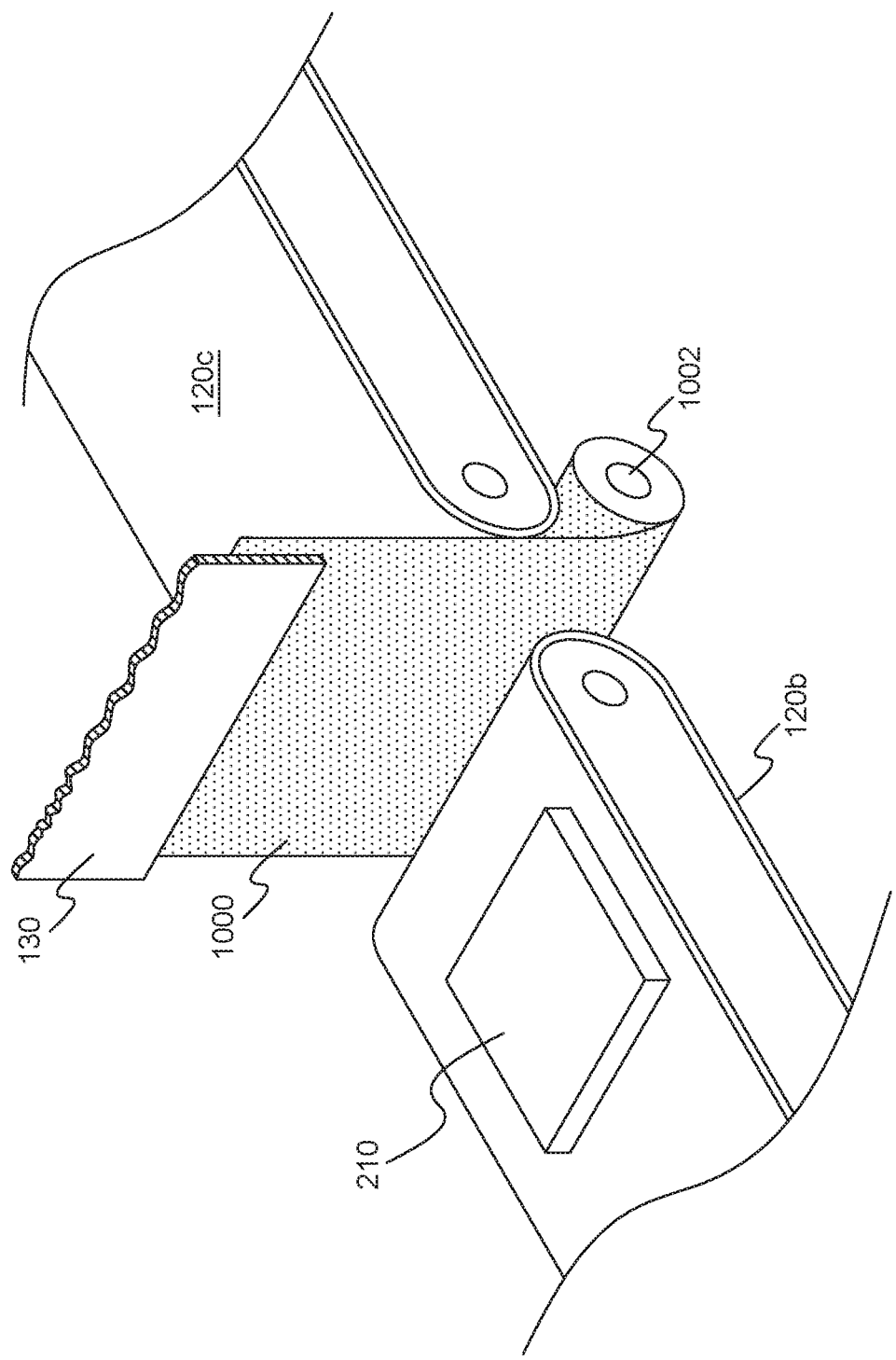
FIG. 10 is an illustration of an embodiment of the cleansing and packaging apparatus illustrating an example supply of packaging material.

In one embodiment, the conveyor system 120 can include the two conveyor sections 120b and 120c, as shown in FIG. 10 that operate in coordination with the three sets of sealing doors, 240, 130 and 140, to commence the packaging operation as the medical instrument exits the cleansing compartment 105. In such an embodiment, conveyor section 120b is configured to convey the instrument to be cleansed into and through the cleansing compartment 105. Conveyor section 102c is configured to convey the cleansed instrument 230 through and out of the packaging compartment 110. In such an example, the sealing joining door component 130 between the two conveyor sections 120b and 120c can be configured to open vertically or horizontally with wrapping material 1000 disposed across the entrance to the packaging compartment 110. In such an example, it is further understood that the sealing joining door component 130 sealingly closes to provide a liquid, air-tight seal at the exit of the cleansing compartment 105 and the entry of the packaging compartment 110.

Referring to FIG. 2, in an exemplary general operation by the example cleansing and packaging system 100, the conveyor system 120 transports a receptacle, such as the example porous instrument tray 210 containing a medical instrument 230 into the sealable cleansing compartment 105. The instrument 230 can, alternatively, be transported by the conveyor system 120 without the instrument tray 210. In such case, the instrument 230 can be placed directly on the conveyor 120. Further, the cleansing and packaging system 100 and the instrument tray 210 may both be configured to accommodate instruments of various dimensions and shapes. The use of a porous instrument tray 210 is preferred to deliver medical instruments into the cleansing and packaging system 100, as illustrated in FIG. 2. However, the instruments of other items to be cleansed and packaged may be placed directly on the conveyor 120 without a porous instrument tray 210.

Referring again to FIG. 2, upon conveying the instrument 230 into the sealable cleansing compartment 105, the sealing entry door component 240 of the cleansing compartment 105 opens to allow the conveyor 120 to convey the instrument 230 to the cleansing position 370, as shown in FIG. 3, inside the cleansing compartment 105. The sealing entry door component 240 is openable to permit the instrument 230 and tray 210 to be conveyed into the cleansing compartment 105 and sealingly closeable to seal the entry into the cleansing compartment 105.

Referring again to FIG. 1, upon departure of the instrument 230 from the cleansing compartment 105, the conveyor 120 transports the tray 210 containing the instrument 230 into the packaging compartment 110 through the sealing joining door component 130, also shown in FIGS. 3 and 4, disposed between the cleansing compartment 105 and the packaging compartment 110. The sealing joining door component 130 opens to allow the conveyor 120 to convey the instrument 230 out of the cleansing position 370, as shown in FIG. 3, inside the cleansing compartment 105 to, for example, a packaging position 470, as shown in FIG. 4, inside the packaging compartment 110. The sealing joining door component 130 is openable to permit the instrument 230 and tray 210 to be conveyed into the packaging compartment 110 and sealingly closeable to seal the entry into the packaging compartment 110.

Referring again to FIG. 1, upon departure of the instrument 230 from the cleansing and packaging system 100, the conveyor system 120 transports the tray 210 containing the instrument 230 within a wrapped package 150 out of the packaging compartment 110 through the sealing exit door component 140 to a container 160 for the wrapped package 150. The sealing exit door component 140 opens to allow the conveyor 120 to convey the instrument 230 out of the packaging position 470, as shown in FIG. 4, inside the packaging compartment 110. The sealing exit door component 140 is openable to permit the instrument 230 and tray 210 to be conveyed out of the packaging compartment 110 and sealingly closeable to seal the exit from the packaging compartment 110.

Referring to FIG. 3, an example cleansing compartment 105 in the example cleansing and packaging system 100 is shown. The cleansing compartment 105 includes both a sanitation system and a sterilization system, together in the same compartment 105. In the example cleansing compartment 105 of FIG. 3, an array of cleansing nozzles is shown for spraying cleansing solution onto an instrument 230 at the cleansing position 370. The cleansing nozzles include upper spray nozzles 320, middle spray nozzles 325, and lower spray nozzles 330. Further, a plurality of inspection devices, including lights 305 and sensors 315, is shown.

The cleansing position 370 is surrounded by the cleansing nozzles and inspection devices. Notably, the inventors have recognized that it would be advantageous to implement automatic inspection using inspection devices, such as the lights 305 and sensors 315, continuously during each sanitation and sterilization operation in the cleansing compartment 105. An automatic inspection system would eliminate the need for manual checks at the beginning and end of each sanitation and sterilization operation.

Those of skill in the art will recognize that inspection capability may be provided by ultraviolet sensors that detect the concentration of hydrogen peroxide based on light from the ultraviolet spectrum, for example. Hydrogen peroxide has specific absorption in ultraviolet light, so detecting areas of low absorption can indicate a lack of such sterilant gas in the cleansing compartment 105. Similarly, other materials such as bleach have florescent properties that can be detected by the automatic inspection system.

Further, those of skill in the art will also recognize the application of three-dimensional imaging as it relates to stereo vision with three-dimensional pattern matching and object tracking, for purposes of sensors used to identify errors in the sanitation and sterilization of medical instruments. In the cleansing compartment 105, three-dimensional cameras can be implemented by utilizing a pair of cameras placed at different locations in the compartment 105. Using a computer algorithm, the three-dimensional cameras provide a stereoscopic view and three-dimensional reconstruction of a sterilant concentration, such as the hydrogen peroxide concentration, at each point inside the cleansing compartment 105 to confirm an appropriate level of sterilant in the compartment 105.

The application of an automatic inspection system, using lights 305 and sensors 315, for pipeline processing inside the example cleansing and packaging system 100 would be advantageous over prior art inspection techniques, such as biological indicators, for example, which require extended periods of time—sometimes days—to indicate whether a sterilization is successful.

In addition, the plurality of inspection devices, such as lights 305 and sensors 315, can be affixed to a rotating mount 335, as shown in FIG. 3, that features the ability to rotate 360 degrees, to provide the lights 305 and sensors 315 an enhanced optical perspective for viewing an instrument 230 in the cleansing position 370 during sanitation and sterilization operations inside the cleansing compartment 105. Further, the mount 335 may feature any number and any combination of inspection devices. For example, the mount 335 may hold four lights 305 and four sensors 315.

It is understood that the cleansing compartment 105 may feature any number and any combination of inspection devices, such as lights 305 and sensors 315. For both the sanitation and sterilization processes within the cleansing compartment 105, the plurality of inspection devices assists in the cleansing process for medical instruments. It is understood that the plurality of inspection devices may include a broad variety of sensors and inspection mechanisms, such as UV sensors, heat seeking detectors, biological indicators, chemical reagents, and humidity detectors.

In the example cleansing compartment 105 shown in FIG. 3, the inspection devices, such as lights 305 and sensors 315, continuously revolve around the interior of the cleansing compartment 105 on the rotating mount 335 for the entire duration of the sanitation and sterilization operations. It is understood that the inspection devices may revolve or move about the interior of the cleansing compartment 105 to visualize an instrument 230 via other patterns of motion and mechanisms of movement.

Focusing now upon an example sanitation operation inside the cleansing compartment 105, reference is made again to FIG. 3, showing an example of the cleansing compartment 105 configured, in part, for sanitation operations. During a sanitation operation, the inspection devices, such as lights 305 and sensors 315, scan the medical instrument 230 after the conveyor system 120 transports the porous tray 210 containing the medical instrument 230 to the cleansing position 370 inside the cleansing compartment 105. The inspection devices continuously scan for defects, such as microbial residue and other debris on the medical instrument 230 to determine the course of the sanitation operation for the medical instrument 230. The inspection devices are continuously inspecting the entire sanitation process from start to finish, and they are continuously revolving about the cleansing compartment 105 on the rotating mount 335 as they inspect, so that they can continuously inspect the sanitation process from multiple angles.

Referring again to FIG. 3 showing the depicted example of a cleansing compartment 105 configured, in part, for sanitation operations, an array of sanitation nozzles is shown. More specifically, FIG. 3 depicts upper spray nozzles 320, middle spray nozzles 325, and lower spray nozzles 330, all surrounding the cleansing position 370. These sanitation nozzles can spray the instrument 230 with a suitable sanitizing agent. As there is a plurality of sanitation nozzles, some of the sanitation nozzles can be designated to spray a particular substance and perform different tasks or pulses at alternating times, depending on the requirements of the sanitation operation. In the example cleansing compartment 105 depicted in FIG. 3, it is understood that all sanitation nozzles can spray the same sanitizing agent, or some sanitation nozzles can spray one substance while other sanitation nozzles can spray a different sanitizing agent. Therefore, several different kinds of sanitizing agents can be sprayed, where each substance can be sprayed by a different sanitation nozzle. Further, it is understood that the cleansing compartment 105 may feature any number and any combination of upper nozzles 320, middle nozzles 325 and lower nozzles 330. In addition, the upper nozzles 320, middle nozzles 325 and lower nozzles 330 can work in conjunction with the inspection devices, such as the lights 305 and sensors 315. For example, in a sanitation operation, the sensors 315 can scan the medical instrument 230 to detect coverage of the sanitizing agent. If the sensors 315 detect that a portion of the instrument 230 is not covered, a further sanitation operation can be conducted where the upper nozzles 320, middle nozzles 325 and lower nozzles 330 spray the instrument 230 with sanitizing agent to confirm coverage of the instrument 230 with the sanitizing agent. Thereafter, the inspection devices may further inspect the instrument 230 to detect and confirm coverage of the instrument 230 with the sanitizing agent.

Further, referring again to FIG. 3, it is understood that the sanitation system of the cleansing compartment 105 may also feature a mechanism, such as sanitation nozzles, configured to rapidly inject fluid to fill the cleansing compartment 105 with a volume of sanitizing fluid 350, where such sanitizing fluid 350 can be introduced to fill the cleansing compartment 105 to a desired level to submerge the instrument 230. Once the instrument 230 is submerged in the volume of sanitizing fluid 350, the plurality of inspection devices, such as lights 305 and sensors 315, that are affixed to the rotating mount 335, may scan and inspect the instrument 230 to confirm that the instrument 230 is sanitized based on various factors. Such factors may include the amount of time the instrument 230 has been submerged in the sanitizing fluid 350 and the absence of sanitation defects, as detected by the inspection devices, such as microbial residue and other debris on the instrument 230. Upon completion of the sanitation operation, the volume of sanitizing fluid 350 may be drained from the cleansing compartment 105 and the spray nozzles may further spray the instrument 230 in coordination with further inspections by the plurality of inspection devices. The inspection devices determine when the sanitation operation is complete and whether additional sanitation operations are required prior to a subsequent sterilization operation.

In addition, it is understood that a cleansing compartment 105 configured, in part, for sanitation operations can include additional components not shown in FIG. 3, such as a dehumidifier, fans, vents, a vacuum pump and a heating element. The cleansing compartment 105 configured, in part, for sanitation operations can include any components required to remove moisture from the cleansing compartment 105 and instrument 230 prior to and upon completion of a sanitation operation. Of course, those of skill in the art would realize that, for certain methods of sterilization, the instrument 230 must be dry before initiating a sterilization operation.

Currently, it is common practice to leave devices to dry in an unconcealed, non-sterile, open-air environment after sanitation. The inventors have recognized that it would be advantageous to implement a faster drying process within a concealed, sterile environment without any exposure to microbial elements from outside air. Various stages of drying the instrument 230 may be implemented, such as blow drying and humidity testing within the cleansing compartment 105 at the cleansing position 370.

Figure 5:
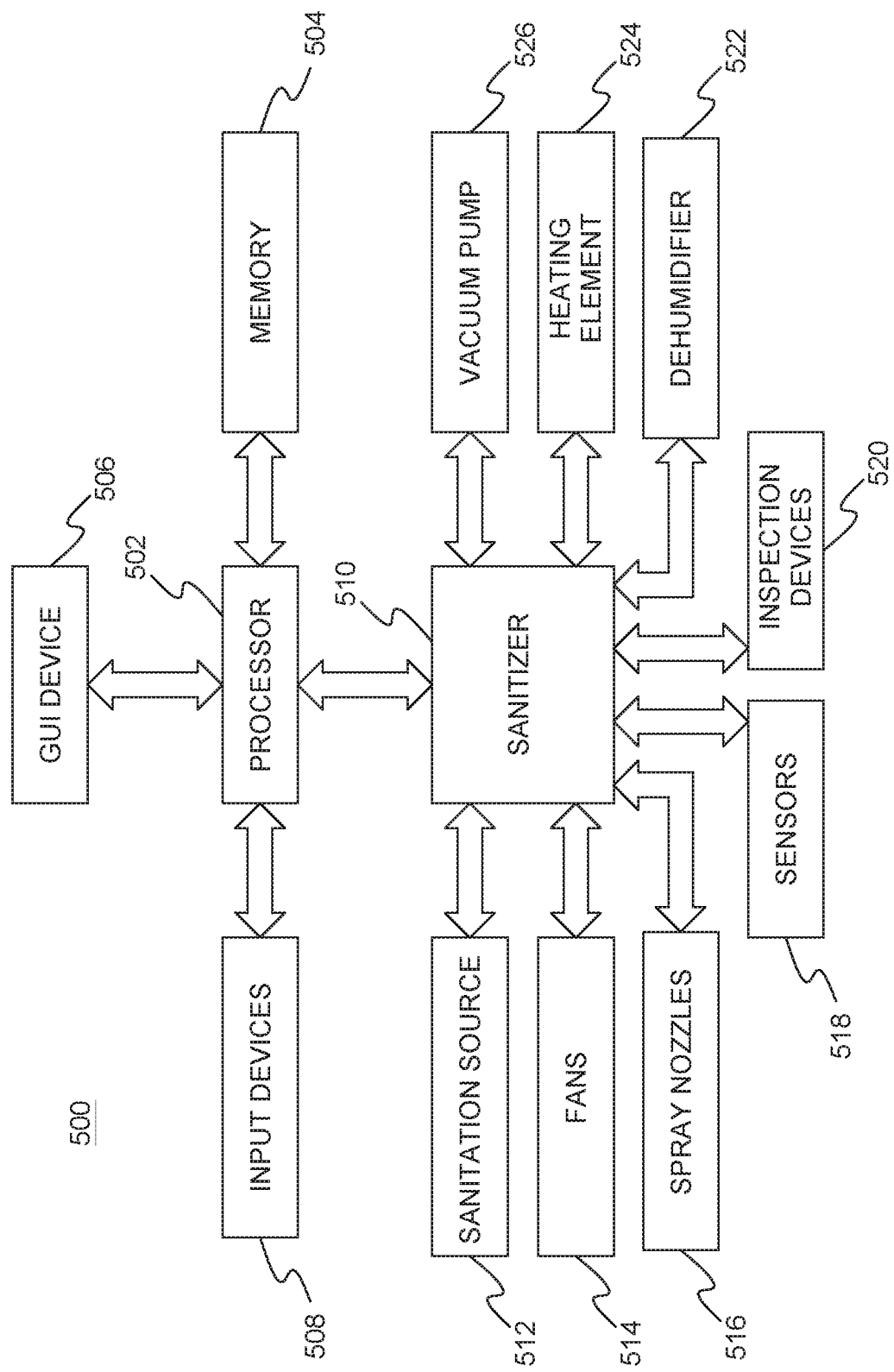
FIG. 5 is a block diagram of an example sanitation system which is used in conjunction with one or more disclosed embodiments.

Referring to FIG. 5, a block diagram shows an example sanitation system 500 in which one or more disclosed embodiments can be implemented. The sanitation system 500 includes a processor 502, a memory 504, a graphical user interface ("GUI") device 506, one or more input devices 508, and a sanitizer 510. The sanitizer 510 may utilize a sanitation source 512, fans 514, spray nozzles 516, sensors 518, inspection devices 520, a dehumidifier 522, a heating element 524, and a vacuum pump 526. It is understood that the sanitation system 500 can include additional components not shown in FIG. 5.

The processor 502 may include a central processing unit (CPU). The memory 504 can be located on the same die as the processor 502, or can be located separately from the processor 502. The memory 504 can include a volatile or non-volatile memory, for example, random access memory (RAM), dynamic RAM, or a cache.

The GUI device 506 uses a visual output for display. The GUI device 506 may also comprise a touch sensitive screen. The input devices 508 may include a keyboard, a keypad, a touch screen, a touch pad, a detector, a microphone, an accelerometer, a gyroscope, a biometric scanner, or a network connection (e.g., a wireless local area network card for transmission and/or reception of wireless IEEE 802 signals). The input devices 508 communicate with the processor 502, and the processor 502 receives input from the input devices 508. The sanitizer 510 produces a sanitation operation, the power of which is controlled by the medical personnel. This permits the medical personnel to determine the parameters of the sanitation operation to be applied to the medical instrument 230, and for how long, to ultimately attain the desired sanitation of the instrument 230.

Figure 6:
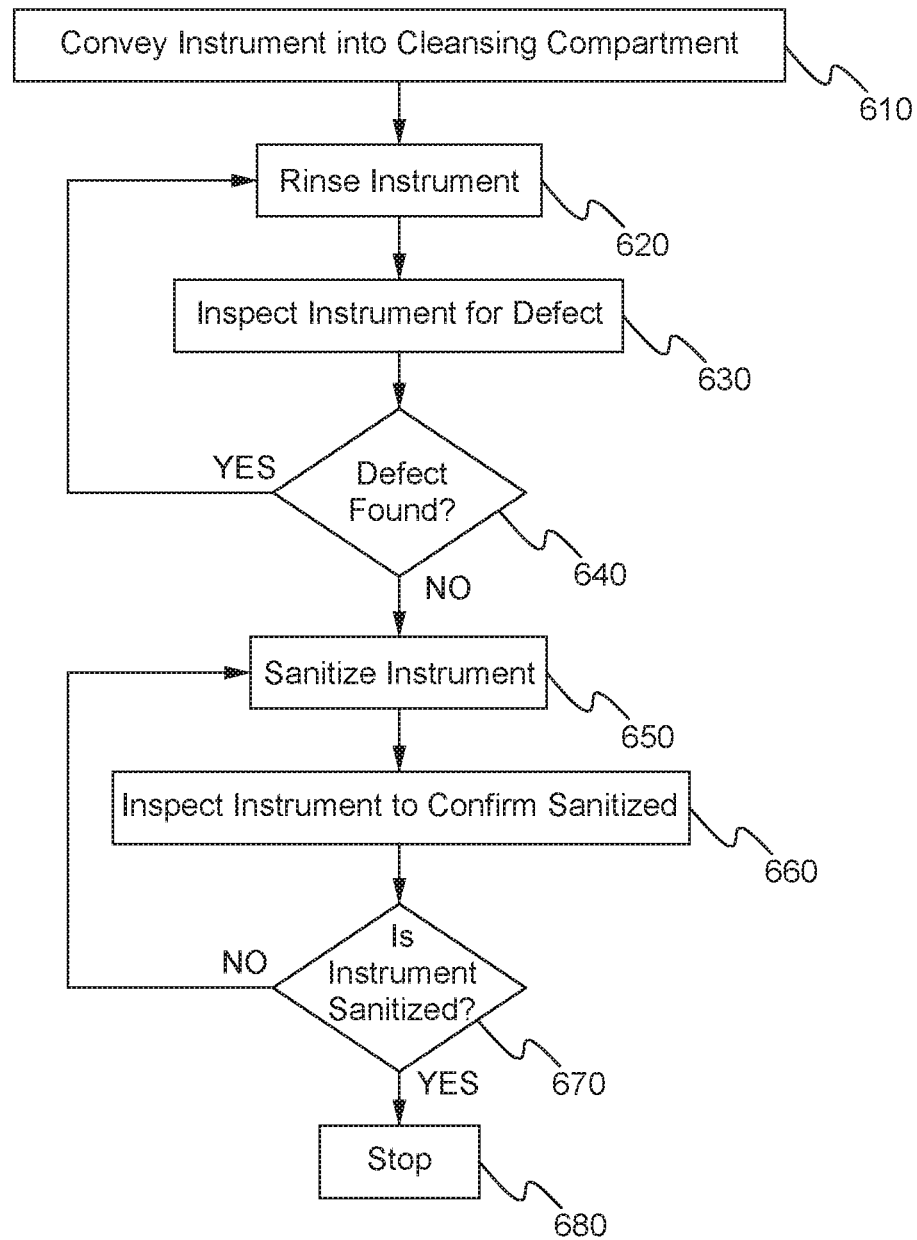
FIG. 6 is a flow diagram of an example sanitation operation which is used in conjunction with one or more disclosed embodiments.

Referring to FIG. 6, a flow diagram illustrates the process 600 of sanitizing the instrument 230 by utilizing a sanitation system 500. As shown in FIG. 6, the process 600 begins 610 by utilizing the conveyor system 120 to transport the tray 210 containing the instrument 230 into the cleansing compartment 105 operable for sanitation inside the cleansing and packaging system 100. The instrument 230 is then rinsed 620 and subsequently inspected 630 for a defect. After the instrument 230 has been inspected 630, a determination will be made whether the instrument 230 has a defect (step 640). For example, a defect at step 640 may be the presence of debris or microbial elements on the instrument 230 as detected by the sensors 315. If the instrument 230 has no defect, then the sanitation system 500 will initiate sanitation of the instrument 230 (step 650). If the instrument 230 still requires additional rinsing to fix a defect, then the sanitation system 500 will again rinse 620 and inspect 630 the instrument 230 until the instrument 230 passes inspection at step 640. Upon completion of sanitation 650, the instrument 230 will be inspected 660 to confirm that the sanitation is complete. A decision will be made as to whether sanitation is successful (step 670). For example, if microbial elements are detected on the instrument 230 by the sensors 315 at step 670, a determination would be made that the instrument is not sanitized. If sanitation is successful, then the sanitation operation is complete (step 680). If the instrument 230 still requires sanitation, then the sanitation system 500 will again sanitize 650 and inspect 660 the instrument 230 until the instrument 230 passes inspection at step 670.

Figure 7:
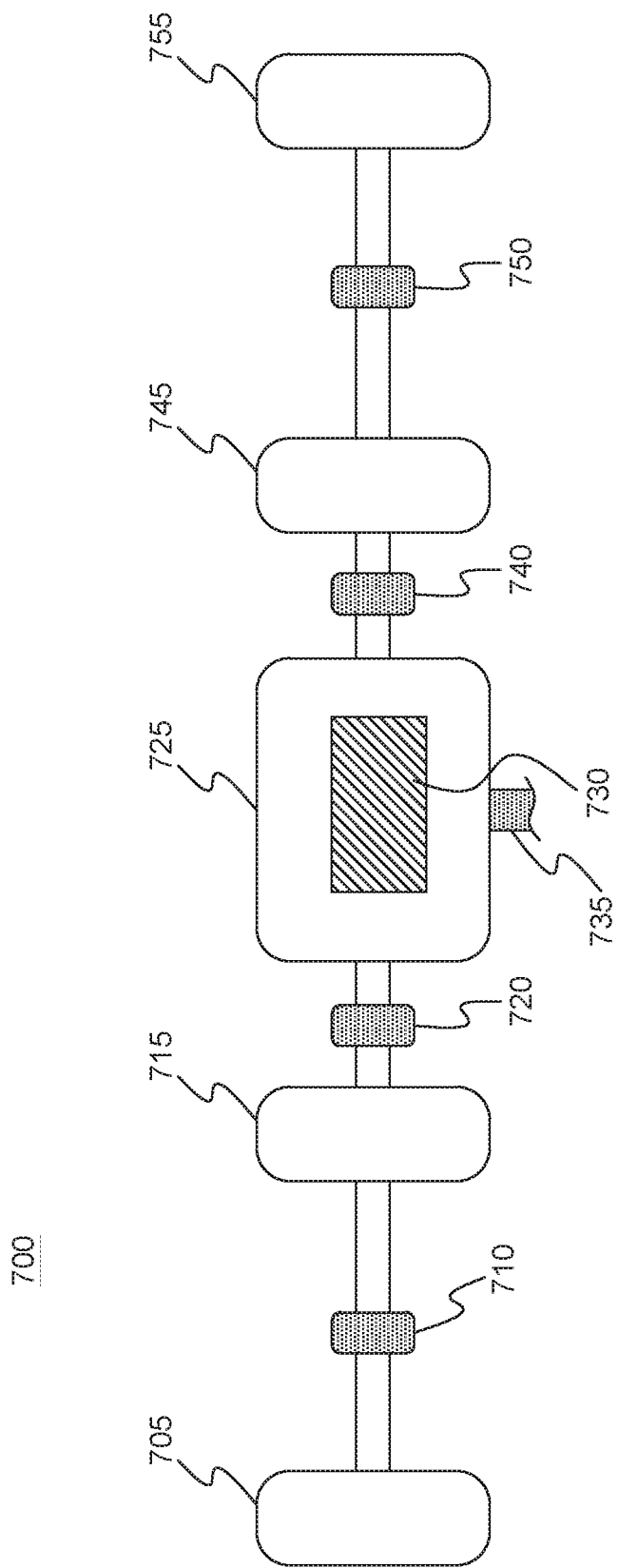
FIG. 7 is a block diagram of an example hydrogen peroxide gas plasma sterilization system which is used in conjunction with one or more disclosed embodiments.

Referring to FIG. 7, what is shown is an example hydrogen peroxide gas plasma sterilization system 700 that may reside within the cleansing compartment 105 of the cleansing and packaging system 100. In a hydrogen gas plasma sterilization system 700, a typical cycle begins when an instrument 230 is surrounded by hydrogen peroxide vapor inside the compartment 105. After the hydrogen peroxide vapor diffuses through the instrument 230, a vacuum mechanism reduces the pressure in the compartment 105 in preparation to generate the hydrogen peroxide gas plasma via the application of radio frequency energy to the compartment 105 from a radio frequency amplifier. It is understood that a cleansing compartment 105 in the cleansing and packaging system 100 can utilize alternative sterilization systems not shown in FIG. 7, including high temperature systems, such as steam and dry heat units, or chemicals, such as ethylene oxide gas, nitrogen dioxide gas, or ozone gas. It is known to sterilize instruments with a vaporized chemical sterilant, such as hydrogen peroxide, peracetic acid, and glutaraldehyde and formaldehyde.

Referring to FIG. 7, a block diagram shows an example hydrogen peroxide gas plasma sterilization system 700, having an injection site 705 for a sterilant source of liquid hydrogen peroxide solution, separated by a first valve 710 from a vaporizer 715 that vaporizes the sterilant. The vaporized sterilant passes a second valve 720 into the sterilization chamber 725, in which the load 730 or porous tray 210 containing the instrument 230 resides. In the application of the example hydrogen peroxide gas plasma sterilization system 700 to the example cleansing and packaging system 100, it is understood that the cleansing compartment 105 of the cleansing and packaging system 100 would constitute the sterilization chamber 725 of the example hydrogen peroxide gas plasma sterilization system 700.

Referring again to FIG. 7, the sterilization chamber 725 may utilize a vent 735, and a third valve 740 separates the chamber 725 from a condenser 745 that condenses the vaporized sterilant. A fourth valve 750 separates the condenser 745 from a vacuum pump 755. The pump 755 creates a vacuum on the chamber 725 to reduce the pressure in the chamber 725 and vaporizer 715. Hydrogen peroxide sterilization cycles, for example, utilize the vacuum pump 755 to create the required low pressure environment for vaporization. The low pressure in the vaporizer 715 assists in the vaporization of the liquid hydrogen peroxide solution. Further, those of skill in the art of hydrogen peroxide gas plasma sterilization would realize that the chamber 725 may include a mechanism, such as a radio frequency amplifier, for production of low frequency voltages or radio frequency voltages to create gas discharge plasma under low pressure conditions.

Focusing now upon an example sterilization operation inside the cleansing compartment 105, reference is made again to FIG. 3, showing the example cleansing compartment 105 configured, in part, for sterilization operations. During a sterilization operation, the inspection devices, such as lights 305 and sensors 315, scan the medical instrument 230 after the conveyor system 120 transports the tray 210 containing a medical instrument 230 to the cleansing position 370 inside the cleansing compartment 105. The inspection devices continuously scan for defects, such as microbial residue and moisture on the medical instrument 230 to determine the most appropriate sterilization operation for the medical instrument 230. The inspection devices are continuously inspecting the entire sterilization process from start to finish, and they are continuously revolving about the cleansing compartment 105 on the rotating mount 335 as they inspect, so that they can continuously inspect the sterilization process from multiple angles. For example, in a hydrogen peroxide gas plasma sterilization operation, the sensors 315 scan the medical instrument 230 to detect coverage of the hydrogen peroxide sterilant. If the sensors 315 detect that a portion of the instrument 230 is not covered, a further sterilization operation can be conducted to confirm coverage of the instrument 230 with the hydrogen peroxide sterilant. Thereafter, the inspection devices may further inspect the instrument 230 to detect and confirm coverage of the instrument 230 with the hydrogen peroxide sterilant.

Further, it is known that for certain methods of sterilization, such as hydrogen peroxide gas plasma sterilization, the instruments must be dry before initiating a sterilization operation. Various stages for drying the instrument 230 may be implemented, such as blow drying and humidity testing within the compartment 105 at the cleansing position 370. Therefore, if the inspection devices detect moisture on the instrument 230 or within the compartment 105, a dehumidifier or other mechanisms for removing moisture within the cleansing compartment 105 may be utilized to dry the instrument 230 prior to the sterilization operation.

In addition, it is understood that a cleansing compartment 105 configured, in part, for sterilization operations can include additional components not shown in FIG. 3, such as valves, a vaporizer, a condenser, a dehumidifier, fans, vents, a vacuum pump, a radio frequency amplifier and a heating element. The cleansing compartment 105 configured, in part, for sterilization operations can include any components required to remove moisture from the cleansing compartment 105 and instrument 230 prior to initiation of a sterilization operation. Of course, those of skill in the art would realize that, for certain methods of sterilization, the instrument 230 must be dry before initiating a sterilization operation.

Referring again to FIG. 3 showing the depicted example of the cleansing compartment 105 configured, in part, for sterilization operations, an array of sterilization nozzles is shown. More specifically, FIG. 3 depicts upper spray nozzles 320, middle spray nozzles 325, and lower spray nozzles 330, all surrounding the cleansing position 370. These sterilization nozzles can spray the instrument 230 with a suitable sterilization agent. As there is a plurality of sterilization nozzles, some of the sterilization nozzles can be designated to spray a particular substance and perform different tasks or pulses at alternating times, depending on the requirements of the sterilization operation. In the example cleansing compartment 105 depicted in FIG. 3 that is configured, in part, for sterilization operations, it is understood that all sterilization nozzles can spray the same sterilization agent, or some sterilization nozzles can spray one agent while other sterilization nozzles spray a different sterilization agent. Therefore, several different kinds of sterilization agents can be sprayed, where each sterilant can be sprayed by a different sterilization nozzle. Further, it is understood that the cleansing compartment 105 may feature any amount and any combination of upper nozzles 320, middle nozzles 325 and lower nozzles 330. In addition, the upper nozzles 320, middle nozzles 325 and lower nozzles 330 can work in conjunction with the inspection devices, such as lights 305 and sensors 315. For example, in a hydrogen peroxide gas plasma sterilization operation, the sensors 315 can scan the medical instrument 230 to detect coverage of the hydrogen peroxide sterilant. If the sensors 315 detect that a portion of the instrument 230 is not covered, a further sterilization operation can be conducted where the upper nozzles 320, middle nozzles 325 and lower nozzles 330 spray the instrument 230 with sterilant to confirm coverage of the instrument 230 with the hydrogen peroxide sterilant. Thereafter, the inspection devices may further inspect the instrument 230 to detect and confirm coverage of the instrument 230 with the hydrogen peroxide sterilant.

Figure 8:
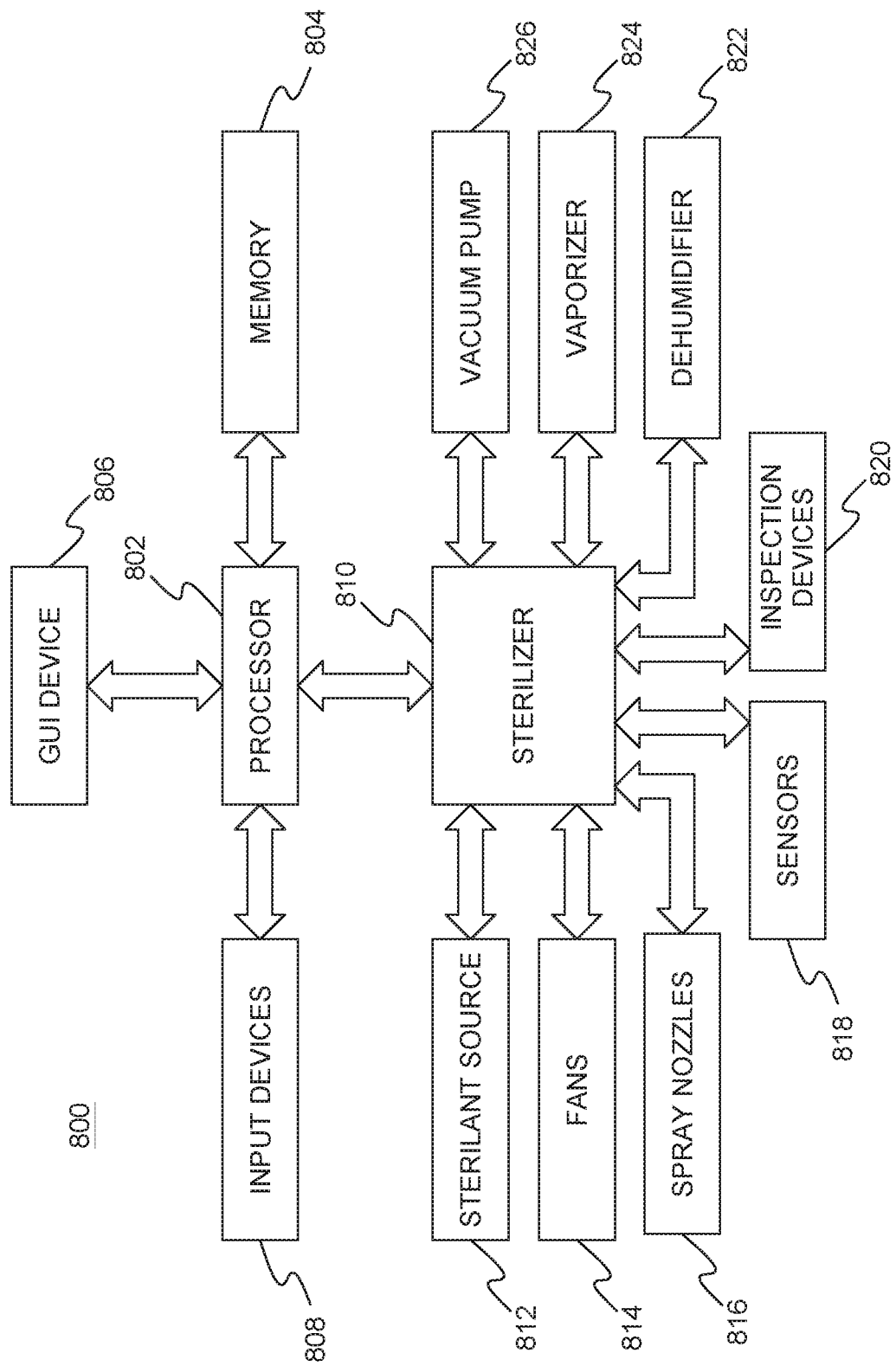
FIG. 8 is a block diagram of an example sterilization system which is used in conjunction with one or more disclosed embodiments.

Referring to FIG. 8, a block diagram shows an example sterilization system 800 in which one or more disclosed embodiments can be implemented. The sterilization system 800 includes a processor 802, a memory 804, a graphical user interface ("GUI") device 806, one or more input devices 808, and a sterilizer 810. The sterilizer 810 may utilize a sterilant source 812, fans 814, spray nozzles 816, sensors 818, inspection devices 820, a dehumidifier 822, a vaporizer 824, and a vacuum pump 826. It is understood that the sterilization system 800 can include additional components not shown in FIG. 8, such as valves, a condenser, vents, a radio frequency amplifier and a heating element.

The processor 802 may include a central processing unit (CPU). The memory 804 can be located on the same die as the processor 802, or can be located separately from the processor 802. The memory 804 can include a volatile or non-volatile memory, for example, random access memory (RAM), dynamic RAM, or a cache.

The GUI device 806 uses a visual output for display. The GUI device 806 may also comprise a touch sensitive screen. The input devices 808 may include a keyboard, a keypad, a touch screen, a touch pad, a detector, a microphone, an accelerometer, a gyroscope, a biometric scanner, or a network connection (e.g., a wireless local area network card for transmission and/or reception of wireless IEEE 802 signals). The input devices 808 communicate with the processor 802, and the processor 802 receives input from the input devices 808. The sterilizer 810 produces a sterilization operation, the power of which is controlled by the medical personnel. This permits the medical personnel to determine the parameters of the sterilization operation to be applied to the medical instrument 230, and for how long, to ultimately attain the desired sterilization of the instrument 230.

Figure 9:
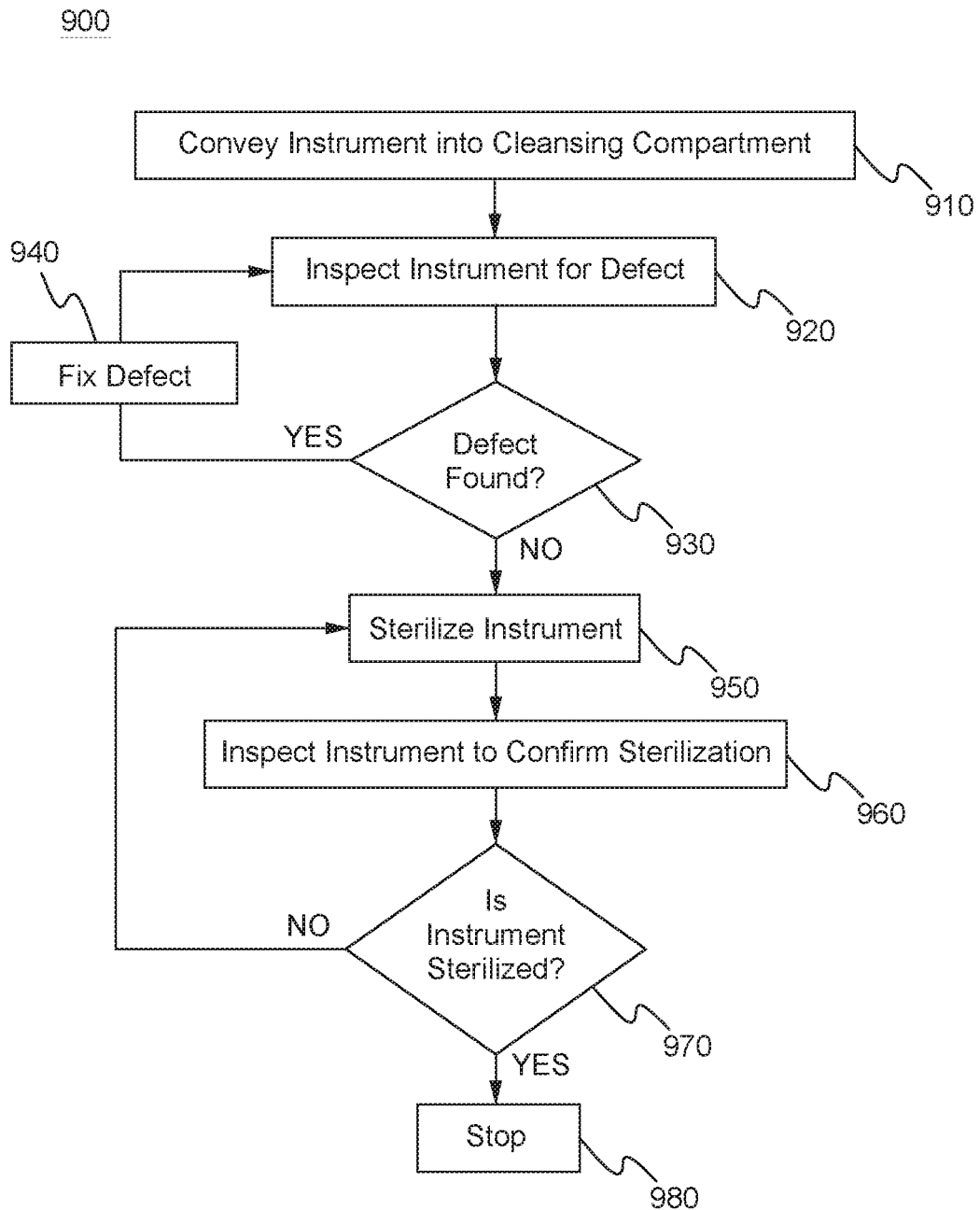
FIG. 9 is a flow diagram of an example sterilization operation which is used in conjunction with one or more disclosed embodiments.

Referring to FIG. 9, a flow diagram illustrates the process 900 of sterilizing the instrument 230 by utilizing a sterilization system 800. As shown in FIG. 9, the process 900 begins 910 by utilizing the conveyor system 120 to transport the tray 210 containing the instrument 230 into a cleansing compartment 105 operable for sterilization inside the cleansing and packaging system 100. The instrument 230 is then inspected for a defect 920. After the instrument 230 has been inspected 920, a determination will be made whether the instrument 230 has a defect (step 930). For example, a defect at step 930 may be the presence of moisture on the instrument 230 or humidity in the cleansing compartment 105, as detected by the sensors 315. If it is determined that the instrument 230 has no defect, then the sterilization system 800 will initiate sterilization of the instrument 230 (step 950). If the instrument 230 has a defect, then the sterilization system 800 will fix the defect 940 and inspect 920 the instrument 230 until the instrument 230 passes inspection at step 930. Upon completion of sterilization 950, the instrument 230 will be inspected 960 to confirm that the sterilization is complete. A decision will be made as to whether sterilization is successful (step 970). As an example of step 970, in a hydrogen peroxide gas plasma sterilization operation, the sensors 315 scan the medical instrument 230 to detect coverage of the hydrogen peroxide sterilant. If the sensors 315 detect that a portion of the instrument 230 is not covered, a further sterilization operation can be conducted to confirm coverage of the instrument 230 with the hydrogen peroxide sterilant. If it is determined at step 970 that sterilization is successful, then the sterilization operation is complete (step 980). If the instrument 230 still requires sterilization, then the sterilization system 800 will again sterilize 950 and inspect 960 the instrument 230 until the instrument 230 passes inspection at step 970.

Therefore, having thus described the components of the cleansing compartment 105 and exemplary sanitation and sterilization operations within the cleansing compartment 105, particular attention will now be focused upon the components of the packaging compartment 110 and an exemplary packaging operation.

Referring to FIG. 4, an example packaging compartment 110 in the example cleansing and packaging system 100 is shown. In the depicted example, the packaging compartment 110 includes a packaging system. A packaging operation begins when the conveyor 120 transports the porous tray 210 containing the medical instrument 230 through the sealing joining door component 130 to the packaging position 470. Those skilled in the art of packaging articles would realize that it is known to package articles, including medical instruments, automatically. Various systems of automatic packaging may be utilized, including vacuum packaging, shrink wrap packaging and semi-permeable sealable pouches. It is understood that the cleansing and packaging system 100 can also include other additional known alternative packaging systems. In one embodiment, the packaging system in the packaging compartment 110 features a mechanism to distribute a piece of packaging material 410 on top of the conveyor 120 and underneath the tray 210 containing the instrument 230 to package the instrument 230. It is known that this mechanism may be achieved by a variety of mechanical mechanisms well known in the art.

For example, with reference to FIG. 10, in one embodiment, packaging can be performed automatically by passing the tray 210 into the packaging compartment 110 and through wrapping material 1000. In such an embodiment, the conveyor system 120 can include the two conveyor sections 120*b* and 120*c*. Conveyor section 120*b* is configured to convey the instrument to be cleansed into and through the cleansing compartment 105. Conveyor section 102*c* is configured to convey the cleansed instrument through and out of the packaging compartment 110. In such an example, the sealing joining door component 130 can be configured to open in connection with the wrapping material 1000 drawn from a supply 1002 of wrapping material 1000 to be disposed in the path of travel of the instrument tray 210.

In operation, after the medical instrument within the tray 210 is cleansed, and preferably dried, the sealing joining door component 130 is raised and conveyor section 120*b* conveys the tray 210 to enter the packaging compartment 110 through the wrapping material 1000 and onto conveyor section 120*c* which completes the transport of the tray 210 covered by the wrapping material 1000 into the packaging compartment 110 for completion of the packaging operation. The wrapping material 1000 can be selectively cut from its supply 1002 and the ends of the wrapping material 1000 can then be secured automatically in a manner to completely wrap the tray 210 having the cleansed medical instrument with conventional packaging apparatus housed within the packaging compartment 110.

Automatic packaging of sterile medical instruments using such wrapping material 1000 drawn from a supply 1002 of wrapping material 1000 is disclosed in U.S. Pat. No. 5,732,529, which is incorporated by reference herein. Those of skill in the art of packaging sterile instruments would understand that the wrapping material 1000 for making sterile packages may be provided on large rolls which are unwound during the feeding of the wrapping material 1000 into the leading edge of the package making equipment. Further, the sealing of unsealed packages of medical instruments is disclosed in U.S. Pat. No. 5,987,855, which is also incorporated by reference herein. It is understood that the packaging compartment 110 may also include sealing dies to apply heat and sealing pressure to an unsealed package. Of course, the packaging compartment 110, as shown in FIGS. 1, 2 and 4, may be configured to accommodate mechanical mechanisms necessary to achieve the sterile, sealed packaging of a medical instrument.

In another embodiment of the packaging compartment 110, it is understood that the packaging compartment 110, as shown in FIG. 4, can include a similar rotating mount 335 holding a plurality of inspection devices, including lights 305 and sensors 315, as shown in FIG. 3. Although the packaging compartment 110 in FIG. 4 has been illustrated without the rotating mount 335 holding a plurality of inspection devices, including lights 305 and sensors 315, as shown in FIG. 3, it is understood that, in another embodiment, the packaging compartment 110 may include the rotating mount 335 holding the plurality of inspection devices. In such an embodiment, the inspection devices may surround the packaging position 470. The inventors have recognized that it can be advantageous to implement automatic inspection using inspection devices, such as the lights 305 and sensors 315, continuously during a packaging operation in the packaging compartment 110. An automatic inspection system can eliminate the need for manual checks at the beginning and end of a packaging operation. Further, those of skill in the art will also recognize the application of three-dimensional imaging as it relates to stereo vision with three-dimensional pattern matching and object tracking, for purposes of sensors used to identify errors in the packaging of medical instruments.

In addition, the rotating mount 335 inside the packaging compartment 110 features the ability to rotate 360 degrees, to provide the attached lights 305 and sensors 315 an enhanced optical perspective for viewing an instrument 230 during a packaging operation. The inspection devices, such as lights 305 and sensors 315, continuously revolve around the interior of the packaging compartment 110 on the rotating mount 335 for the entire duration of a packaging operation. It is understood that the inspection devices may revolve or move about the interior of the packaging compartment 110 to visualize an instrument 230 via other patterns of motion and mechanisms of movement. Further, the mount 335 may feature any number and any combination of inspection devices. For example, the mount 335 may hold four lights 305 and four sensors 315. For a packaging processes within the packaging compartment 110, the plurality of inspection devices assists in the packaging process for medical instruments.

In addition, it is understood that a packaging compartment 110 can include additional components not shown in FIG. 4, such as a dehumidifier, fans, vents, a vacuum pump and a heating element. The packaging compartment 110 can include any components required to remove moisture from the packaging compartment 110 and instrument 230 prior to and upon completion of a packaging operation. Because an instrument 230 must be dry before initiating a packaging operation, it is understood that that various stages of drying the instrument 230 may be implemented, such as blow drying and humidity testing within the compartment 110.

Figure 11:
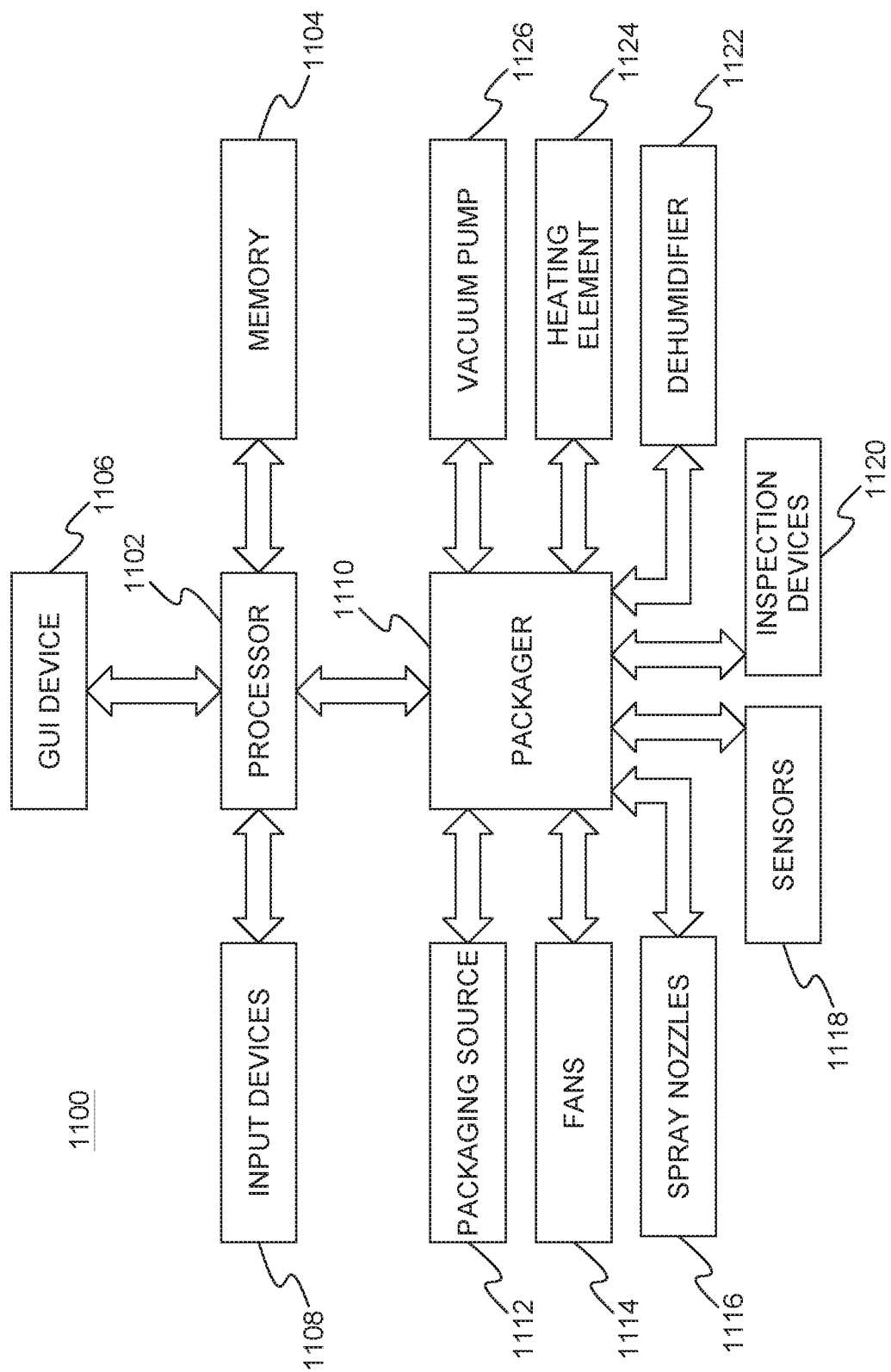
FIG. 11 is a block diagram of an example packaging system which is used in conjunction with one or more disclosed embodiments.

Referring to FIG. 11, a block diagram shows an example packaging system 1100 in which one or more disclosed embodiments can be implemented. In one embodiment, the packaging system 1100 packages a tray 210 containing a medical instrument 230 while in the packaging position 470. In another embodiment, the packaging system 1100 packages only the medical instrument 230, itself, without including the tray 210 inside the package. When packaging is complete, the conveyor system 120 can transport the tray 210 containing the instrument 230 away from the packaging position 470 and out of the packaging compartment 110 through the sealing exit door component 140, shown in FIG. 1.

Referring again to FIG. 11, the block diagram shows an example packaging system 1100 that includes a processor 1102, a memory 1104, a graphical user interface ("GUI") device 1106, one or more input devices 1108, and a packager 1110. The packager 1110 may utilize a packaging source 1112, fans 1114, spray nozzles 1116, sensors 1118, inspection devices 1120, a dehumidifier 1122, a heating element 1124, and a vacuum pump 1126. It is understood that the packaging system 1100 can include additional components not shown in FIG. 11.

The processor 1102 may include a central processing unit (CPU). The memory 1104 can be located on the same die as the processor 1102, or can be located separately from the processor 1102. The memory 1104 can include a volatile or non-volatile memory, for example, random access memory (RAM), dynamic RAM, or a cache.

The GUI device 1106 uses a visual output for display. The GUI device 1106 may also comprise a touch sensitive screen. The input devices 1108 may include a keyboard, a keypad, a touch screen, a touch pad, a detector, a microphone, an accelerometer, a gyroscope, a biometric scanner, or a network connection (e.g., a wireless local area network card for transmission and/or reception of wireless IEEE 802 signals). The input devices 1108 communicate with the processor 1102, and the processor 1102 receives input from the input devices 1108. The packager 1110 produces a packaging operation, the power of which is controlled by the medical personnel. This permits the medical personnel to determine the parameters of the packaging operation to be applied to the medical instrument 230, and for how long, to ultimately attain the desired packaging of the instrument 230.

Figure 12:
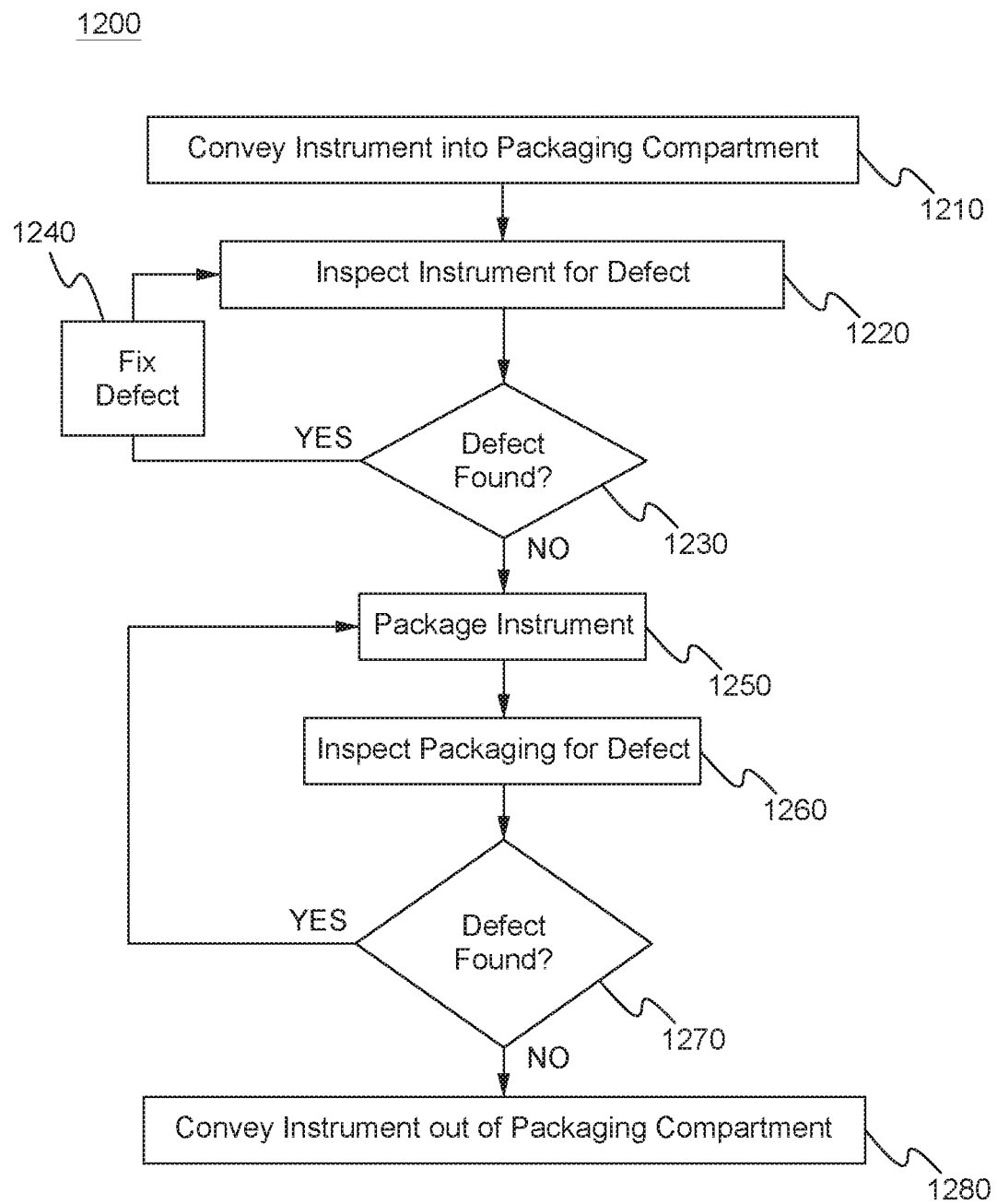
FIG. 12 is a flow diagram of an example packaging operation which is used in conjunction with one or more disclosed embodiments.

Referring to FIG. 12, a flow diagram illustrates the process 1200 of packaging the instrument 230 by utilizing a packaging system 1100. As shown in FIG. 12, the process 1200 begins 1210 by utilizing the conveyor system 120 to transport the tray 210 containing the instrument 230 into a packaging compartment 110 inside the cleansing and packaging system 100. The instrument 230 is then inspected for a defect 1220. After the instrument 230 has been inspected 1220, a determination will be made whether the instrument 230 contains a defect (step 1230). For example, a defect at step 1230 may be the presence of moisture on the instrument 230 or humidity in the packaging compartment 110, as detected by the sensors 315. If it is determined that the instrument 230 has no defect, then the packaging system 1100 will initiate packaging of the instrument 230 (step 1250). If the instrument 230 has a defect, then the packaging system 1100 will fix the defect 1240 and inspect 1220 the instrument 230 until the instrument 230 passes inspection at step 1230. Upon completion of packaging 1250, the instrument 230 will be inspected 1260 to confirm that the packaging is complete and has no defect. A decision will be made as to whether there is a defect in the packaging (step 1270). For example, a defect at step 1270 may be the presence of a hole in the packaging material 410 or wrapping material 1000 or humidity in the packaging compartment 110, as detected by the sensors 315. If packaging is successful, the process is complete (step 1280), and the conveyor system 120 will transport the tray 210 containing the instrument 230 out of the packaging compartment 110 inside the cleansing and packaging system 100. If the instrument 230 still requires packaging due to a defect in the packaging, then the packaging system 1100 will again package 1250 and inspect 1260 the instrument 230 until the instrument 230 passes inspection at step 1270.

Figure 13:
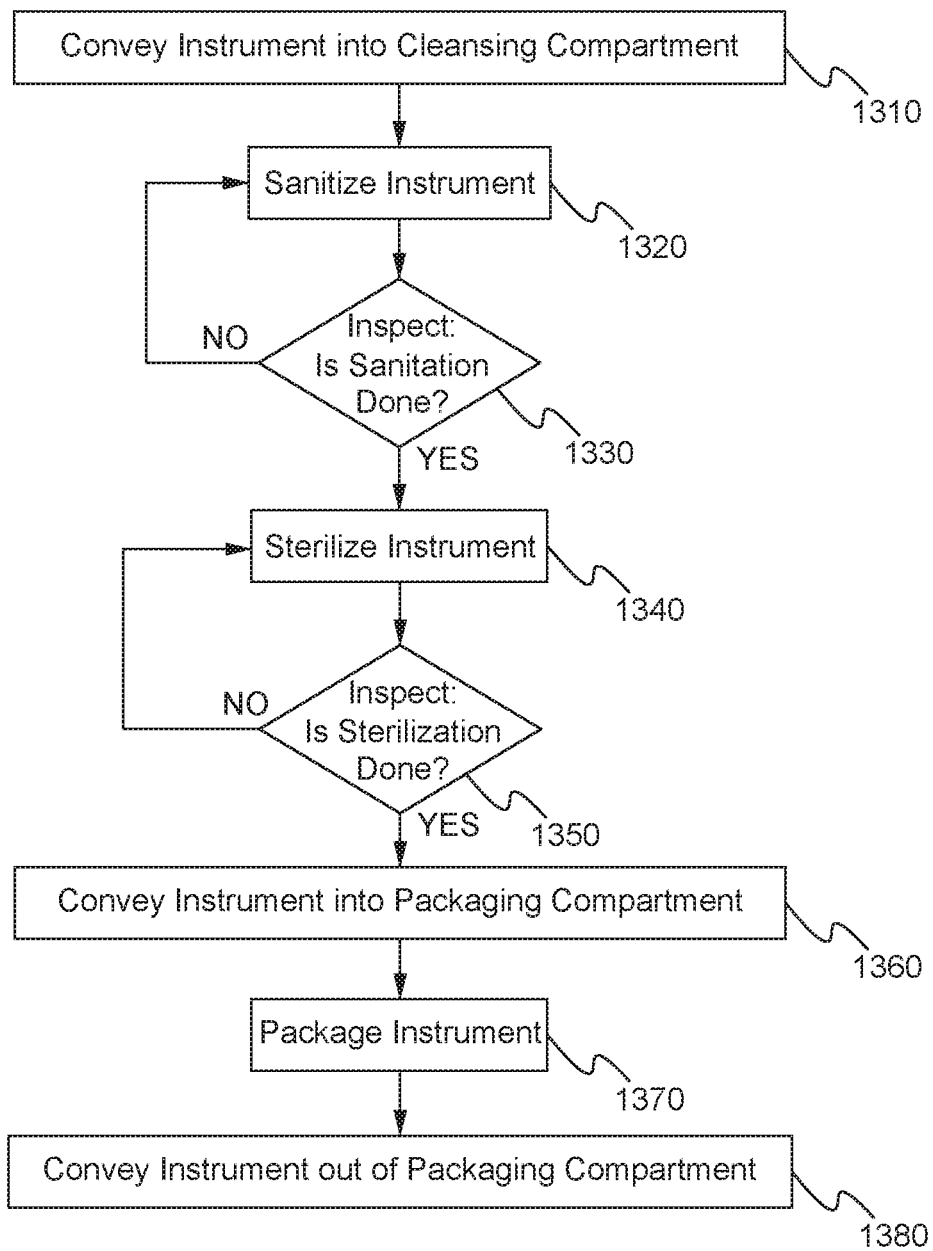
FIG. 13 is a flow diagram of an example procedure combining the sanitation, sterilization and packaging processes, which is used in conjunction with one or more disclosed embodiments.

Of course, in another embodiment, the aforementioned processes of sanitation, sterilization and packaging can all be performed together in one process, within the cleansing and packaging system 100. Referring to FIG. 13, a flow diagram illustrates the process 1300 of sanitizing, sterilizing and packaging the instrument 230 by utilizing a sanitation system 500, sterilization system 800, and packaging system 1100. As shown in FIG. 13, the process 1300 begins 1310 by utilizing the conveyor system 120 to transport the tray 210 containing the instrument 230 into a cleansing compartment 105 operable for sanitation and sterilization inside the cleansing and packaging system 100. The instrument 230 is then sanitized 1320. After the instrument 230 has been sanitized 1320, an inspection will be made to determine whether the instrument 230 has been successfully sanitized (step 1330). If it is determined that the instrument 230 has been successfully sanitized, then the instrument 230 is then sterilized 1340. If the instrument 230 has not been successfully sanitized, then the sanitation system 500 will sanitize the instrument again 1320 and inspect 1330 the instrument 230 until the instrument 230 passes inspection at step 1330. After the instrument 230 has been sterilized 1340, an inspection will be made to determine whether the instrument 230 has been successfully sterilized (step 1350). If it is determined that the instrument 230 has been successfully sterilized, then the conveyor system 120 will transport the tray 210 containing the instrument 230 into a packaging compartment 110 operable for packaging inside the cleansing and packaging system 100 (step 1360). If the instrument 230 has not been successfully sterilized, then the sterilization system 800 will sterilize the instrument again 1340 and inspect 1350 the instrument 230 until the instrument 230 passes inspection at step 1350. The instrument 230 is then packaged 1370. After the instrument 230 has been packaged 1370, then the conveyor system 120 will transport the tray 210 containing the instrument 230 out of the packaging compartment 110 operable for packaging inside the cleansing and packaging system 100 (step 1380).

What is claimed is:

1. An apparatus for cleansing and packaging items, including, but not limited to, medical instruments, comprising:
 a first sealable compartment housing a cleansing device;
 a second sealable compartment joined to the first compartment housing a packaging device; and
 a conveyor device configured to selectively transport items to be cleansed and packaged through the first compartment and second compartment;
 the conveyor and compartments configured to:
  convey an item to be cleansed and packaged into the first compartment to a cleansing position where the first compartment is sealed from external contamination for the cleansing device to cleanse the conveyed item;
  convey the cleansed item from the first compartment directly into the second compartment where the second compartment is sealed from external contamination for the packaging device to package the cleansed item; and
  convey the cleansed and packaged item from the second compartment, wherein:
 the cleansing device includes a sanitation device and a sterilization device;
 the sanitation device includes a plurality of sanitation nozzles configured for spraying at least one solution onto an item disposed at the cleansing position; and
 the sterilization device includes a plurality of sterilization nozzles configured for spraying at least one solution onto an item disposed at the cleansing position.

2. The apparatus of claim 1, wherein:
 the first compartment is configured with a sealing entry door component;
 the second compartment is configured with a sealing exit door component;
 a sealing joining door component is provided for communication between the first and second compartments;
 the entry door component configured to open for conveying an item to the cleansing position and to sealingly close when the item is disposed at the cleansing position;
 the joining door component configured to be sealingly closed when the item is disposed at the cleansing position and during cleansing, to open for conveying a cleansed item into the second compartment; and
 the exit door component configured to be sealingly closed during packaging of the item and to open to permit the cleansed, packaged item to exit.

3. The apparatus of claim 1, wherein the sterilization device includes one or more of the following:
  a hydrogen peroxide gas plasma sterilization system;
  an ethylene oxide gas sterilization system;
  an ozone gas sterilization system;
  a nitrogen dioxide gas sterilization system;
  a hydrogen peroxide gas sterilization system;
  a peracetic acid gas sterilization system;
  a formaldehyde gas sterilization system; or
  a glutaraldehyde gas sterilization system.

4. The apparatus of claim 1, wherein the packaging device includes a drying device configured to dry an item and the packaging device is operable to dry an item before and/or after a packaging operation.

5. The apparatus of claim 1, wherein the cleansing device includes cleansing sensors configured to detect cleansing defects and the cleansing device is operable to sense cleansing defects of an item after a cleansing operation and to conduct a further cleansing operation if a cleansing defect is sensed.

6. An apparatus for cleansing and packaging items, including, but not limited to, medical instruments, comprising:
  a first sealable compartment housing a cleansing device;
  a second sealable compartment joined to the first compartment housing a packaging device; and
  a conveyor device configured to selectively transport items to be cleansed and packaged through the first compartment and second compartment;
  the conveyor and compartments configured to:
    convey an item to be cleansed and packaged into the first compartment to a cleansing position where the first compartment is sealed from external contamination for the cleansing device to cleanse the conveyed item;
    convey the cleansed item from the first compartment directly into the second compartment where the second compartment is sealed from external contamination for the packaging device to package the cleansed item; and
    convey the cleansed and packaged item from the second compartment, wherein:
  the cleansing device includes a sanitation device and a sterilization device;
  the sanitation device includes a drying device configured to dry an item and the sanitation device is operable to dry an item before and/or after a sanitation operation; and
  the sterilization device includes a drying device configured to dry an item and the sterilization device is operable to dry an item before and/or after a sterilization operation.

7. The apparatus of claim 6, wherein:
  the first compartment is configured with a sealing entry door component;
  the second compartment is configured with a sealing exit door component;
  a sealing joining door component is provided for communication between the first and second compartments;
  the entry door component configured to open for conveying an item to the cleansing position and to sealingly close when the item is disposed at the cleansing position;
  the joining door component configured to be sealingly closed when the item is disposed at the cleansing position and during cleansing, to open for conveying a cleansed item into the second compartment; and
  the exit door component configured to be sealingly closed during packaging of the item and to open to permit the cleansed, packaged item to exit.

8. The apparatus of claim 6, wherein the sterilization device includes one or more of the following:
  a hydrogen peroxide gas plasma sterilization system;
  an ethylene oxide gas sterilization system;
  an ozone gas sterilization system;
  a nitrogen dioxide gas sterilization system;
  a hydrogen peroxide gas sterilization system;
  a peracetic acid gas sterilization system;
  a formaldehyde gas sterilization system; or
  a glutaraldehyde gas sterilization system.

9. The apparatus of claim 6, wherein the cleansing device includes a plurality of cleansing nozzles for spraying at least one solution onto an item disposed at the cleansing position.

10. The apparatus of claim 6, wherein the packaging device includes a drying device configured to dry an item and the packaging device is operable to dry an item before and/or after a packaging operation.

11. The apparatus of claim 6, wherein the cleansing device includes cleansing sensors configured to detect cleansing defects and the cleansing device is operable to sense cleansing defects of an item after a cleansing operation and to conduct a further cleansing operation if a cleansing defect is sensed.

12. An apparatus for cleansing and packaging items, including, but not limited to, medical instruments, comprising:
  a first sealable compartment housing a cleansing device;
  a second sealable compartment joined to the first compartment housing a packaging device; and
  a conveyor device configured to selectively transport items to be cleansed and packaged through the first compartment and second compartment;
  the conveyor and compartments configured to:
    convey an item to be cleansed and packaged into the first compartment to a cleansing position where the first compartment is sealed from external contamination for the cleansing device to cleanse the conveyed item;
    convey the cleansed item from the first compartment directly into the second compartment where the second compartment is sealed from external contamination for the packaging device to package the cleansed item; and
    convey the cleansed and packaged item from the second compartment, wherein:
  the cleansing device includes a sanitation device and a sterilization device;
  the sanitation device includes sanitation sensors configured to detect sanitation defects and the sanitation device is operable to sense sanitation defects of an item after a sanitation operation and to conduct a further sanitation operation if a sanitation defect is sensed; and
  the sterilization device includes sterilization sensors configured to detect sterilization defects and the sterilization device is operable to sense sterilization defects of an item after a sterilization operation and to conduct a further sterilization operation if a sterilization defect is sensed.

13. The apparatus of claim 12, wherein:
  the sanitation device includes a rotational mount configured to hold the sanitation sensors and the sanitation device is operable to continuously rotate the mount holding the sanitation sensors 360 degrees during a sanitation operation; and the sterilization device includes a rotational mount configured to hold the sterilization sensors and the sterilization device is operable to continuously rotate the mount holding the sterilization sensors 360 degrees during a sterilization operation.

14. The apparatus of claim 12, wherein:
the first compartment is configured with a sealing entry door component;
the second compartment is configured with a sealing exit door component;
a sealing joining door component is provided for communication between the first and second compartments;
the entry door component configured to open for conveying an item to the cleansing position and to sealingly close when the item is disposed at the cleansing position;
the joining door component configured to be sealingly closed when the item is disposed at the cleansing position and during cleansing, to open for conveying a cleansed item into the second compartment; and
the exit door component configured to be sealingly closed during packaging of the item and to open to permit the cleansed, packaged item to exit.

15. The apparatus of claim 12, wherein the sterilization device includes one or more of the following:
a hydrogen peroxide gas plasma sterilization system;
an ethylene oxide gas sterilization system;
an ozone gas sterilization system;
a nitrogen dioxide gas sterilization system;
a hydrogen peroxide gas sterilization system;
a peracetic acid gas sterilization system;
a formaldehyde gas sterilization system; or
a glutaraldehyde gas sterilization system.

16. The apparatus of claim 12, wherein the cleansing device includes a plurality of cleansing nozzles for spraying at least one solution onto an item disposed at the cleansing position.

17. The apparatus of claim 12, wherein the packaging device includes a drying device configured to dry an item and the packaging device is operable to dry an item before and/or after a packaging operation.

18. A method for cleansing and packaging items, including, but not limited to, medical instruments, comprising:
providing a first sealable compartment housing a cleansing device, a second sealable compartment joined to the first compartment housing a packaging device, and a conveyor device configured to selectively transport items to be cleansed and packaged through the first compartment and the second compartment;
conveying an item to be cleansed and packaged into the first compartment to a cleansing position where the first compartment is sealed from external contamination for the cleansing device to cleanse the conveyed item;
conveying the cleansed item from the first compartment directly into the second compartment where the second compartment is sealed from external contamination for the packaging device to package the cleansed item; and
conveying the cleansed and packaged item from the second compartment, wherein the cleansing device includes a sanitation device and a sterilization device, the sanitation device includes a plurality of sanitation nozzles configured for spraying at least one solution onto an item disposed at the cleansing position and the sterilization device includes a plurality of sterilization nozzles configured for spraying at least one solution onto an item disposed at the cleansing position, further comprising:
conducting a sanitation operation followed by a sterilization operation to cleanse an item disposed at the cleansing position;
spraying at least one solution onto an item disposed at the cleansing position during a sanitation operation; and
spraying at least one solution onto an item disposed at the cleansing position during a sterilization operation.

19. The method of claim 18, wherein the first compartment is configured with a sealing entry door component, the second compartment is configured with a sealing exit door component, and a sealing joining door component is provided for communication between the first and second compartments, further comprising:
opening the entry door component for conveying an item to the cleansing position;
closing the entry door component when the item is disposed at the cleansing position;
having the joining door component sealingly closed when the item is disposed at the cleansing position during cleansing of the item;
opening the joining door component for conveying the cleansed item into the second compartment;
having the exit door component sealingly closed during packaging of the item; and
opening the exit door component to permit the cleansed, packaged item to exit.

20. The method of claim 18, wherein the sterilization device includes one or more of the following:
a hydrogen peroxide gas plasma sterilization system;
an ethylene oxide gas sterilization system;
an ozone gas sterilization system;
a nitrogen dioxide gas sterilization system;
a hydrogen peroxide gas sterilization system;
a peracetic acid gas sterilization system;
a formaldehyde gas sterilization system; or
a glutaraldehyde gas sterilization system;
further comprising:
conducting a sanitation operation followed by a sterilization operation to cleanse an item disposed at the cleansing position.

21. The method of claim 18, wherein the packaging device includes a drying device configured to dry an item in the second compartment, further comprising:
conducting a packaging operation to package an item in the second compartment; and
drying an item in the second compartment before and/or after a packaging operation.

22. The method of claim 18, wherein the cleansing device includes cleansing sensors configured to detect cleansing defects, further comprising:
sensing cleansing defects of an item after a cleansing operation and conducting a further cleansing operation if a cleansing defect is sensed.

23. A method for cleansing and packaging items, including, but not limited to, medical instruments, comprising:
providing a first sealable compartment housing a cleansing device, a second sealable compartment joined to the first compartment housing a packaging device, and a conveyor device configured to selectively transport items to be cleansed and packaged through the first compartment and the second compartment;
conveying an item to be cleansed and packaged into the first compartment to a cleansing position where the first compartment is sealed from external contamination for the cleansing device to cleanse the conveyed item;

conveying the cleansed item from the first compartment directly into the second compartment where the second compartment is sealed from external contamination for the packaging device to package the cleansed item; and conveying the cleansed and packaged item from the second compartment, wherein the cleansing device includes a sanitation device and a sterilization device, the sanitation device includes a drying device configured to dry an item disposed at the cleansing position and the sterilization device includes a drying device configured to dry an item disposed at the cleansing position, further comprising:

conducting a sanitation operation followed by a sterilization operation to cleanse an item disposed at the cleansing position;

drying an item disposed at the cleansing position before and/or after a sanitation operation; and drying an item disposed at the cleansing position before and/or after a sterilization operation.

24. The method of claim 23, wherein the first compartment is configured with a sealing entry door component, the second compartment is configured with a sealing exit door component, and a sealing joining door component is provided for communication between the first and second compartments, further comprising:

opening the entry door component for conveying an item to the cleansing position;

closing the entry door component when the item is disposed at the cleansing position;

having the joining door component sealingly closed when the item is disposed at the cleansing position during cleansing of the item;

opening the joining door component for conveying the cleansed item into the second compartment;

having the exit door component sealingly closed during packaging of the item; and opening the exit door component to permit the cleansed, packaged item to exit.

25. The method of claim 23, wherein the sterilization device includes one or more of the following:

a hydrogen peroxide gas plasma sterilization system;
an ethylene oxide gas sterilization system;
an ozone gas sterilization system;
a nitrogen dioxide gas sterilization system;
a hydrogen peroxide gas sterilization system;
a peracetic acid gas sterilization system;
a formaldehyde gas sterilization system; or
a glutaraldehyde gas sterilization system;
further comprising:

conducting a sanitation operation followed by a sterilization operation to cleanse an item disposed at the cleansing position.

26. The method of claim 23, wherein the cleansing device includes a plurality of cleansing nozzles configured to spray at least one solution onto an item disposed at the cleansing position, further comprising:

spraying at least one solution onto an item disposed at the cleansing position during a cleansing operation.

27. The method of claim 23, wherein the packaging device includes a drying device configured to dry an item in the second compartment, further comprising:

conducting a packaging operation to package an item in the second compartment; and drying an item in the second compartment before and/or after a packaging operation.

28. The method of claim 23, wherein the cleansing device includes cleansing sensors configured to detect cleansing defects, further comprising:

sensing cleansing defects of an item after a cleansing operation and conducting a further cleansing operation if a cleansing defect is sensed.

29. A method for cleansing and packaging items, including, but not limited to, medical instruments, comprising:

providing a first sealable compartment housing a cleansing device, a second sealable compartment joined to the first compartment housing a packaging device, and a conveyor device configured to selectively transport items to be cleansed and packaged through the first compartment and the second compartment;

conveying an item to be cleansed and packaged into the first compartment to a cleansing position where the first compartment is sealed from external contamination for the cleansing device to cleanse the conveyed item;

conveying the cleansed item from the first compartment directly into the second compartment where the second compartment is sealed from external contamination for the packaging device to package the cleansed item; and conveying the cleansed and packaged item from the second compartment, wherein the cleansing device includes a sanitation device and a sterilization device, the sanitation device includes sanitation sensors configured to detect sanitation defects and the sterilization device includes sterilization sensors configured to detect sterilization defects, further comprising:

conducting a sanitation operation followed by a sterilization operation to cleanse an item disposed at the cleansing position;

sensing sanitation defects of an item after a sanitation operation and conducting a further sanitation operation if a sanitation defect is sensed; and sensing sterilization defects of an item after a sterilization operation and conducting a further sterilization operation if a sterilization defect is sensed.

30. The method of claim 29, wherein the sanitation device includes a rotational mount configured to hold the sanitation sensors and the sterilization device includes a rotational mount configured to hold the sterilization sensors, further comprising:

rotating the mount holding the sanitation sensors 360 degrees continuously during a sanitation operation; and rotating the mount holding the sterilization sensors 360 degrees continuously during a sterilization operation.

31. The method of claim 29, wherein the first compartment is configured with a sealing entry door component, the second compartment is configured with a sealing exit door component, and a sealing joining door component is provided for communication between the first and second compartments, further comprising:

opening the entry door component for conveying an item to the cleansing position;

closing the entry door component when the item is disposed at the cleansing position;

having the joining door component sealingly closed when the item is disposed at the cleansing position during cleansing of the item;

opening the joining door component for conveying the cleansed item into the second compartment;

having the exit door component sealingly closed during packaging of the item; and opening the exit door component to permit the cleansed, packaged item to exit.

32. The method of claim 29, wherein the sterilization device includes one or more of the following:
- a hydrogen peroxide gas plasma sterilization system;
- an ethylene oxide gas sterilization system;
- an ozone gas sterilization system;
- a nitrogen dioxide gas sterilization system;
- a hydrogen peroxide gas sterilization system;
- a peracetic acid gas sterilization system;
- a formaldehyde gas sterilization system; or
- a glutaraldehyde gas sterilization system;

further comprising:
- conducting a sanitation operation followed by a sterilization operation to cleanse an item disposed at the cleansing position.

33. The method of claim 29, wherein the cleansing device includes a plurality of cleansing nozzles configured to spray at least one solution onto an item disposed at the cleansing position, further comprising:
- spraying at least one solution onto an item disposed at the cleansing position during a cleansing operation.

34. The method of claim 29, wherein the packaging device includes a drying device configured to dry an item in the second compartment, further comprising:
- conducting a packaging operation to package an item in the second compartment; and
- drying an item in the second compartment before and/or after a packaging operation.

* * * * *

UNITED STATES PATENT AND TRADEMARK OFFICE
CERTIFICATE OF CORRECTION

PATENT NO. : 10,647,461 B2
APPLICATION NO. : 15/602739
DATED : May 12, 2020
INVENTOR(S) : Andres Claudio Altmann et al.

It is certified that error appears in the above-identified patent and that said Letters Patent is hereby corrected as shown below:

On the Title Page

In Item (57), under "ABSTRACT", in Column 2, Line 12, delete "each which" and insert -- each of which --, therefor.

In the Specification

In Column 7, Line 37, delete "seat" and insert -- seal. --, therefor.

Signed and Sealed this
Sixth Day of December, 2022

Katherine Kelly Vidal
*Director of the United States Patent and Trademark Office*